(12) United States Patent
Ben-Nissan et al.

(10) Patent No.: US 7,258,898 B2
(45) Date of Patent: Aug. 21, 2007

(54) PROCESSES FOR TREATING CORAL AND COATING AN OBJECT

(75) Inventors: Besim Ben-Nissan, Rose Bay (AU);
Adriyan S. Milev, Strathfield (AU);
Douglas Drysdal Green, Mosman (AU); Ji Hu, Korgarah (AU); Robert M. Conway, Annandale (AU); G. S. Kamall Kannangara, Blacktown (AU); Jennifer Russell, Bexley (AU); Edit Gillott, Drummoire (AU); Clifford Trefry, Rodd Point (AU)

(73) Assignee: Nanocoatings Pty, Ltd., New York Wales (AU)

( * ) Notice: Subject to any disclaimer, the term of this patent is extended or adjusted under 35 U.S.C. 154(b) by 554 days.

(21) Appl. No.: 10/416,920

(22) PCT Filed: Nov. 14, 2001

(86) PCT No.: PCT/AU01/01481
§ 371 (c)(1),
(2), (4) Date: Dec. 29, 2003

(87) PCT Pub. No.: WO02/40398
PCT Pub. Date: May 23, 2002

(65) Prior Publication Data
US 2004/0091547 A1    May 13, 2004

(30) Foreign Application Priority Data
Nov. 16, 2000   (AU)   ................................. PR1521

(51) Int. Cl.
*B05D 3/04*    (2006.01)
*B05D 3/10*    (2006.01)

(52) U.S. Cl. .................. 427/301; 427/299; 427/304; 427/314; 427/316; 423/305

(58) Field of Classification Search ............... 427/301, 427/299, 304, 314, 316; 423/305
See application file for complete search history.

(56) References Cited

U.S. PATENT DOCUMENTS 3,929,971 A    12/1975   Roy (Continued)

FOREIGN PATENT DOCUMENTS

JP    10-245525    *   9/1998

(Continued)

OTHER PUBLICATIONS

Gross et al., (Thin hydroxyapatite coatings via sol-gel synthesis, Journal of Materials Science: Materials in Medicine (1998), 9(12), 839-843).*

(Continued)

Primary Examiner—Thurman K. Page
Assistant Examiner—Chukwuma Nwaonicha
(74) Attorney, Agent, or Firm—Nixon & Vanderhye

(57) ABSTRACT

The present invention generally relates to an improved process for the hydrothermal conversion of coral into hydroxyapatite, a process for coating an object with hydroxyapatite, a process for coating an object with a divalent metal phosphate and uses of objects prepared by these processes. Following the processes according to the present invention, the resultant hydroxyapatite has greater strength and bioactivity than that of the coral prior to its conversion.

15 Claims, 16 Drawing Sheets

U.S. PATENT DOCUMENTS

| | | | |
|---|---|---|---|
| 4,861,733 A | 8/1989 | White | |
| 4,938,938 A | 7/1990 | Ewers et al. | |
| 4,976,736 A | 12/1990 | White et al. | |

FOREIGN PATENT DOCUMENTS

| | | | |
|---|---|---|---|
| WO | WO 01/28919 A1 | 4/2001 | |

OTHER PUBLICATIONS

Roy and Linnehan; "Hydroxyapatite formed from Coral Skeletal Carbonate by Hydrothermal Exchange"; (1974); Nature vol. 247; pp. 220-222.

M. Sivakumar et al; "Development of Hydroxyapatite Derived from Indian Coral"; (1996); Biomaterials vol. 17, No. 17; pp. 1709-1714.

J. Hu et al; "Production and Analysis of Hydroxyapatite from Australian Corals via Hydrothermal Process"; pp. 53-55; Dept. of Chemistry, Materials & Forensic Science; Univ. of Technology, Sydney, Australia; Australian Inst. of Marine Science, Townsville, Australia.

L. Jinling et al; Preparing Technology for Changing Coral into Hydroxy Apatite; (1997); EspaceNet CN 1163094; (abstract).

C. Wenjing; "Method for Preparing Hydroxy Phosphatic Rock"; (1997); EspceNet CN 1161305; (abstract).

* cited by examiner

COMPARATIVE NATURAL CORAL, CONVERTED CORAL and CONVERTED and COATED CORAL MECHANICAL PROPERTIES BY BIAXIAL TESTING

| Sample | Dimensions (mm) | Dimensions (mm) | Thickness (mm) | Load P (N) | σ (N/mm²) |
|---|---|---|---|---|---|
| Coral non converted | | | | | |
| 1 | 29.7 | 30.5 | 4.02 | 52 | 5.1 |
| 2 | 30.6 | 29.7 | 3.80 | 83 | 9.4 |
| 3 | 30.2 | 30.7 | 4.34 | 61 | 5.0 |
| Average = 6.5 | | | | | |
| Coral Hydro-thermally converted to Hydroxyapatite | | | | | |
| 1 | 26.1 | 26.0 | 5.48 | 130 | 6.2 |
| 2 | 25.9 | 25.2 | 2.88 | 35 | 7.7 |
| 3 | 26.1 | 26.2 | 3.72 | 67 | 8.1 |
| 4 | 25.9 | 26.1 | 3.26 | 52 | 8.5 |
| Average = 7.6 | | | | | |
| Coral Hydrothermally Converted, Coated and Fired at 900 for 2hours | | | | | |
| 1 | 26.0 | 25.1 | 4.42 | 94 | 7.5 |
| 2 | 25.9 | 25.1 | 2.24 | 50 | 19.8 |
| 3 | 26.1 | 26.1 | 2.00 | 34 | 17.4 |
| 4 | 26.0 | 26.1 | 3.38 | 58 | 8.8 |
| Average = 13.3 | | | | | |

PROCESSES FOR TREATING CORAL AND COATING AN OBJECT

FIELD OF THE INVENTION

This application is the U.S. national phase of international application PCT/AU01/01481, filed 14 Nov. 2001, which designated the U.S.

The present invention generally relates to a process for the conversion of coral into hydroxyapatite, a process for coating an object with hydroxyapatite, a process for coating an object with a divalent metal phosphate and uses of objects prepared by these processes. Following the processes according to the present invention, the resultant hydroxyapatite has greater strength than that of the coral prior to its conversion.

BACKGROUND ART

Hydroxyapatite and related calcium phosphates have been known for many years as being suitable materials for prosthetic implants. In large part, this is due to their similarity with the mineral phase of bone. As it turns out, such materials, and especially hydroxyapatite, are widely used as bone substitutes in oral, periodontal and craniofacial surgery, and increasingly now there is a growing interest for their use in orthopaedic applications such as bone replacements, spinal fusions, joint surgery and the like.

From the point of view of biocompatibility, hydroxyapatite seems to be the most suitable ceramic material for hard tissue replacement implants. Importantly, such ceramics, along with others, do not exhibit any cytotoxic effects.

Over the years, various methods have been developed for the production of hydroxyapatite. One fairly successful approach has involved the hydrothermal conversion of corals. Indeed, it is well-known to convert coral to hydroxyapatite via hydrothermal conversion.

Corals were first converted using the hydrothermal method in 1974 by Roy and Linnehan [D M Roy (1974) "Hydroxyapatite formed from Coral Skeletal Carbonate by Hydrothermal Exchange 247 *Nature*, 220-222]. According to that experiment, complete replacement of aragonite by phosphatic material was achieved at a temperature of 270° C. and a pressure of 103 MPa. However, the Roy method has the disadvantage that the hydrothermal treatment must be carried out at a relatively high temperature and pressure, and the resultant hydroxyapatite may have reduced strength.

But it is not only with the Roy method that the resultant hydroxyapatite has been fragile. Clearly, where the hydroxyapatite is to be used for the development of prosthetic implants, it is undesirable to have excessive fragility.

In 1990, U.S. Pat. No. 4,938,938 disclosed a new method for the hydrothermal conversion process which included a series of cleansing steps to remove impurities from the coral prior to conversion. The disclosure of that specification suggests that the inclusion of such cleansing steps allows for a process with reduced energy requirements and relatively low pressure, which can be carried out over a relatively short period of time, and is nevertheless capable of providing a resultant hydroxyapatite with a desirable bone-like defect density and cryptocrystallinity.

Later the same year, U.S. Pat. No. 4,976,736 also disclosed a process for the production of hydroxyapatite which could be performed at lower temperatures and pressures than that of the process described by Roy. The citation provides a detailed analysis of the way hydroxyapatite formed according to the invention can be used during oral, periodontal, craniofacial and orthopaedic surgery. The real thrust of the invention, is the creation of a material having a base portion of calcium carbonate and a surface layer of a synthetic phosphate, including in some embodiments, hydroxyapatite. Apparently, where bone substitutes are produced according to this invention, it is essentially possible to 'pre-programme' the rate at which the ceramic implant degrades, and, therefore, possible to provide surgeons with a choice as to the rate at which the bone substitute is resorbed following implantation.

More recently in 1996, Sivakumar et al. (17 *Biomaterials* 1709) developed a new method for the hydrothermal conversion of Indian corals.

Owing to the unfavourable mechanical properties of porous hydroxyapatite (HAp), almost all research to date has been focused on the development of calcium phosphate coatings and particulate reinforced composites. Sol gel technology offers an improved alternative technique for producing bioactive surfaces for better bone attachment. Previously published works indicate that although biphasic hydroxyapatite products are available, monophasic hydroxyapatite powders and coatings were difficult to produce.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

DISCLOSURE OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present inventors have found an improved method for the production of hydroxyapatite through the hydrothermal conversion of coral in which the hydroxyapatite produced has particularly desirable properties for use in prosthetic implants.

The present inventors have also found a process for coating an object with a divalent metal phosphate and a process for coating an object with hydroxyapatite. They have found that it is possible to prepare an object having high purity, enhanced durability and strength by utilising a new coral double conversion technique. The two stages of the double conversion technique include (i) preparation of a hydroxyapatite object by hydrothermal conversion of coral, followed by (ii) coating the object with hydroxyapatite or some other divalent metal phosphate according to the invention.

The present inventors have also discovered new phosphonate compounds, new divalent metal phosphonate complexes, methods for their formation and a process for preparing crystalline monophasic divalent metal phosphates which are utilised in one of the processes for coating an object according to the present invention.

The present inventors have found that powder production of divalent metal phosphates, such as hydroxyapatite, according to the present invention is particularly useful in industrial, chemical and pharmaceutical applications.

In a first aspect, the present invention consists in a process for the preparation of a hydroxyapatite material by means of hydrothermal conversion, the process comprising the following steps:
(a) providing a sample of coral;
(b) applying a series of pre-conversion steps to the sample, the pre-conversion steps including:
   (i) treating the sample to remove impurities therefrom;
   (ii) heating the treated sample to a temperature of at least about 50° C. for at least about 3 hours; and
   (iii) washing the heated sample, and then drying the sample;
(c) applying a series of hydrothermal conversion steps to the sample, the hydrothermal conversion steps including:
   (i) placing the sample from step (b)(iii) in a reactor, and treating that sample with a solution of $[(NH_4)_2 HPO_4]$, at a temperature of at least about 150° C. and at a pressure of at least about 1 MPa for at least about 12 hours; and
   (ii) washing the sample, and then drying the sample.

The coral used in the hydrothermal conversion is preferably of the genus Goniopora ($CaCO_3$) or similar. An appropriate sample for preferred embodiments is obtained from the Great Barrier Reef, off the coast of Queensland, Australia. In alternative embodiments, however, the coral used may be of the Genus Alveopora, Arcopora or some other genera of coral. It may, of course, be obtained from any marine site where such coral can be found.

The hydroxyapatite resulting from the treatment of coral according to this invention may be used as a material in the manufacture and/or development of a range of products in which the presence of hydroxyapatite is appropriate and/or desirable. However, since hydroxyapatite can have a porous structure and is biocompatible, the present invention is particularly valuable in the production of hydroxyapatite for use in prosthetic implants. Such prostheses can range frown joint replacements to ocular implants. Indeed, it is well known that porous surfaces on prosthetic implants are valuable in promoting tissue integration (eg muscle binding and bone ingrowth) with the implant.

The pre-conversion steps are preferably used to cleanse the coral sample, and, as will become clear below, to prepare the sample in such a way that following hydrothermal conversion, the resultant hydroxyapatite has greater structural strength than that of the original coral.

In cases where the specific purpose for which the hydroxyapatite is to be formed is known, for example, where it is known that the hydroxyapatite will be used in the manufacture of an ocular implant, the sample can be shaped appropriately at various stages throughout the process. While a substantially spherical shape is appropriate for an ocular implant, the sample should be adapted to the shape most appropriate for the purpose for which it will be used. In a preferred embodiment, the coral sample undergoes initial shaping prior to commencement of the pre-conversion steps (ie prior to step (b), including between steps (a) and (b) above). In a further preferred embodiment, if necessary, the shape of the sample is altered to its final appropriate shape following the completion of the entire process (ie after step (c)(ii) has been completed). In an alternative embodiment, however, the shape of the sample may be changed any one of a number of times throughout the process.

The step of treating the sample to remove impurities therefrom (ie step b(i)) can comprise a series of steps.

In a first cleansing step, the sample is preferably treated with water at a temperature of no less than about 70° C. The temperature of the water may, of course, vary, and can be anywhere between about 70° C. and about 100° C. In a most preferred embodiment, the water is brought to or close to boiling point for the purpose of carrying out this step. In addition, the sample can be treated with the water for no less than about 3 minutes, but can be treated for up to 30 minutes, or even several hours. Most preferably, boiling water is applied to the sample for about 10 minutes.

As a further component of this first cleansing step, the coral sample is preferably subjected to treatment in an ultrasonic bath. In a preferred embodiment, the ultrasonic bath may last anywhere from between a few seconds and several hours, more preferably between about 30 seconds and about 5 minutes, and most preferably for about 2 minutes.

In a second cleansing step, the sample (already treated by the first cleansing step) is then rinsed with water. The water used in the first two cleansing steps is preferably fresh, double distilled, water. In an alternative embodiment, however, the water is not double distilled: it may, in fact, be substituted by some other composition which would serve the purpose of the water in each of the individual steps in which it is used.

In one embodiment of a third cleansing step, the sample is then subjected to a single repeat of the first and second cleansing steps. The third cleansing step can also comprise a plurality of repeats of the first and second cleansing steps. In an alternative embodiment, the first and second cleansing steps can be only performed once, in which case this third cleansing step is omitted from the process altogether.

In a fourth cleansing step the sample, as treated by the first three cleansing steps, is immersed in a solution of NaClO. It is preferred that the solution contains at least about 1% NaClO, more preferably between about 2% to about 15% NaClO and most preferably about 5% NaClO. The duration for which this immersion takes place can range from anywhere between 1 hour and several days. However, the sample is preferably immersed in the NAClO solution for between about 16 and 32 hours, more preferably about 24 hours.

In a fifth cleansing step, the sample is then subjected to a further repeat of the first and second cleansing steps. Like with the third cleansing step, the sample may be subjected to either a single repeat of these steps, or a plurality of such repeats.

A final sixth cleansing step can be performed. This can comprise drying the sample, following its treatment by the earlier cleansing step. The drying can be performed at ambient temperature. Such drying is, however, preferably performed at a temperature of between about 50° C. and about 90° C., but is most preferably performed at about 70° C. The sample is preferably dried over a period of between about 1 hour to several days, more preferably for about 12 hours.

Step (b)(ii) involves heating the cleansed sample to at least about 50° C. The sample is preferably heated to anywhere between about 50° C. and about 600° C., and more preferably to a temperature of between about 200° C. and 400° C., with the most preferred temperature being about 300° C. The sample may, of course, be heated to such a temperature by immediate exposure to the temperature at which the sample is to be heated. More preferably, however, the sample is heated slowly at a steady rate of anywhere between about 1° C. and 50° C. per minute, with a particular preference for about 5° C./minute. The rate of increase in temperature may be constant or variable. Either way, the duration for which the rate of temperature is changing will depend on the temperature to which the sample is to be heated. Similarly, the duration for which the sample is maintained at a particular temperature will also vary depending on the selected temperature. In a most preferred embodiment, the sample is heated to about 300° C. at a constant rate of about 5° C./minute and then held at about 300° C. for about 12 hours.

Heating the coral in step (b)(ii) helps to ensure that the coral's porous structure and strength is retained despite the shaping, washing, cleansing, rinsing and drying to which it is subjected prior to the heating. The fact that the coral is so heated prior to hydrothermal conversion additionally results in increased strength in the sample following the hydrothermal conversion according to the steps which are included in step (c) above.

It is important to note that the temperature at which the sample is heated as well as the rate of such heating according to this step, will depend on the sample size. In one example, where the size of the sample is between about 1 g and about 3 g, the sample is preferably heated to about 300° C. at a constant rate of about 5° C./minute and then held at about 300° C. for about 12 hours. In another example, where the size of the sample is between about 4 g and about 10 g, heat treatment is preferably carried out twice with washing between each heating session. Where the sample size is about 8 g, the heating of step (b)(ii) preferably involves.

(I) heating the sample to about 300° C. at a constant rate of about 5° C./min for about 12 hours;
(II) cooling the heated sample;
(III) washing the cooled sample in boiling water;
(IV) cleansing the washed sample in an ultrasonic bath and washing the cleansed sample; and
(V) heating the sample from (IV) to about 300° C. at a constant rate of about 5° C./min, and keeping the sample at that temperature for about 3 hours.

In this embodiment, the additional heating step provides adequate cleansing for larger samples.

The heating provided in step (b)(ii), is preferably carried out in a tube furnace, but may be carried out in any other appropriate heating apparatus.

The final pre-conversion step—step (b)(iii)—preferably involves washing the sample in water and then drying the sample. The water can be at a temperature anywhere from about 50° C. to about 100° C., but is preferably boiling when the sample is washed according to this step. The sample can be allowed to dry at ambient temperature or dried more quickly at an elevated temperature.

The hydrothermal conversion steps are used to convert the coral structure ($CaCO_3$) to hydroxyapatite [$Ca_{10}(PO_4)_6(OH)_2$].

As described in the first aspect of the invention, the sample of coral which has been treated in accordance with the pre-conversion steps is then treated, at appropriate atmospheric conditions, with a solution of $(NH_4)_2HPO_4$. In preferred embodiments, the solution is supersaturated and has a Ca/P mol ratio of between about 5/20 and about 15/20, with a particular preference for about 10/20. Preferably, the resulting hydrothermally converted material has a Ca/P mol ratio of between about 1.4 to 1.75, more preferably about 1.67.

Like with the heating step of (b)(ii) of the first aspect of the invention, it is important to note that numerous variations for this ratio may be more appropriate in different circumstances, for example, where the sample size is different. Indeed, by way of example, where the size of the sample is from about 1 g to about 3 g, the preferable Ca/P mol ratio is about 10/12, and where the sample size is from about 4 g to about 10 g, the preferable Ca/P mol ratio is about 10/18. In preferred embodiments, the Ca/P mol ratio is varied according to the circumstances of the case.

The reactor in which the sample is placed for hydrothermal conversion (step (c)(i)) is most preferably a Micro Reactor, such as that of Parr Instrument Company, USA (300 ml). A further preferred feature of the reactor is that it has a liner, and most preferably a polytetrafluoroethylene (PTFE) liner. The liner may also be a specific metal appropriate for the environment or gold coated stainless steel. Other reactors with different liners or no liners may also be used.

The preferred atmospheric conditions for carrying out step (c)(i) disclose: a temperature ranging from anywhere between about 100° C. and about 400° C., more preferably between about 200° C. and about 300° C., and most preferably at about 250° C.; and a pressure ranging from anywhere between about 0.5 MPa and about 7 MPa, more preferably between about 2 MPa and about 4 MPa, and most preferably at about 3.8 MPa. In addition, the sample should be kept at these atmospheric conditions for anywhere between about 2 hours and several days, more preferably between about 16 hours and about 32 hours, and most preferably for about 24 hours.

In the final hydrothermal conversion step—step (c)(ii)—the sample is preferably washed by subjecting the sample to a single repeat of the first and second cleansing steps. This step can comprise a plurality of repeats of the first and second cleansing steps, rather than a single repeat. As an additional component to this step, the washed sample is then dried at a temperature anywhere between ambient temperature to about 150° C., more preferably between about 60° C. to about 80° C., and most preferably, the sample is dried at about 70° C. Drying, according to this step, is carried out for a period of anywhere between about 1 hour and several days, more preferably between about 8 hours and about 24 hours, and most preferably for about 12 hours.

According to the most preferred embodiment, all of the most preferred components and apparatus discussed above are utilised, and all the quantities for each of the compositions, temperatures, etc., accord with the figures disclosed by the most preferred embodiments of the invention, rather than their disclosed approximations. In such an embodiment, the final product is preferably pure monophasic hydroxyapatite. Naturally, where alternatives for the components, figures, etc. are utilised, the final product may have a different composition.

In a second aspect, the present invention is directed to a prosthetic implant formed from the hydroxyapatite material prepared according to the first aspect of the invention.

In one embodiment, the prosthetic implant is a dental implant, or an orthopaedic implant such as a joint replacement, a craniofacial implant or an ocular implant.

In another aspect, the present invention is also directed to a bone graft formed from the hydroxyapatite material prepared according to the first aspect of the invention.

The present inventors have investigated alkoxide and mixed alkoxide-salt based sols and the existing methods suitable for preparation of both powders and coatings and found that the intermediate products formed in the early stages of the liquid state (sol) have crucial influence on the purity of hydroxyapatite. It has been found that a critical factor in determining the purity of the final product was the period between solution preparation and its application referred as "ageing of the sols".

The present inventors have carried out extensive studies in relation to the "ageing of sols", a phrase which the present inventors have recognised as meaning the time required for ligand substitution. More specifically, the present inventors have surprisingly found that reaction of calcium diethoxide or calcium acetate with diethyl hydrogen phosphonate in acetic acid/glycol under certain conditions produces diacetyl hydrogen phosphonate and calcium diacetyl hydrogen phosphonate (a precursor to hydroxyapatite). The present inventors have recognised that the so-called "ageing period" is connected with ligand exchange between the ethoxy groups of diacetyl hydrogen phosphonate and the acetate ions of acetic acid and subsequent chelation with $Ca^{2+}$ ions.

A comprehensive chemical characterisation of the intermediates formed during the period referred to as the "ageing of the sols" and subsequent solid state transformations has not only shed light on the mechanism of the sol-gel process but has also provided a reliable method to optimise the conditions to obtain a uniform monophasic hydroxyapatite product.

The present inventors have surprisingly found that the formation of diacetyl hydrogen phosphonate and subsequent formation of calcium diacetyl hydrogen phosphonate complex is very important to the purity of the final hydroxyapatite product. The present inventors have found that two different calcium diacetyl hydrogen phosphonate complexes form and that these complexes allow the ratio of 5/3 or 1.67 between Ca/P to be kept until the precursor decomposes to form hydroxyapatite. If complete conversion to diacetyl hydrogen phosphonate did not take place, the phosphorous precursor is volatilised at elevated temperatures resulting in a change in the Ca/P ratio and a loss of purity in the final hydroxyapatite product due to the formation of CaO.

The present inventors have recognised that the formation of divalent metal complexes of phosphonates with keto groups in a β-position relative to the phosphoryl group may be important in forming pure compounds having structural features and lattice parameters similar to that of hydroxyapatite.

In a third aspect, the present invention is directed to a phosphonate compound according to formula (1);

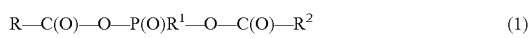

wherein R, $R^1$ and $R^2$, which may be the same or different, are selected from the group consisting of hydrogen, substituted alkyl groups and unsubstituted alkyl groups.

Preferably, R and $R^2$ are alkyl groups, more preferably C1-C6 unsubstituted allyl groups and $R^1$ is hydrogen. Most preferably, R and $R^2$ are $CH_3$ and $R^1$ is hydrogen such that the compound according to formula (1) is diacetyl hydrogen phosphonate.

In a fourth aspect, the present invention is directed to a divalent metal phosphonate complex wherein a divalent metal is coordinated to the phosphonate compound according to the third aspect of the invention.

The divalent metal may be selected from the group consisting of calcium, magnesium, strontium, copper, manganese and zinc although it will be appreciated that any other divalent metal capable of coordinating with the phosphonate compound of formula (I) may be used. Preferably, the divalent metal is calcium.

The divalent metal phosphonate complex may involve coordination of the divalent metal with the carbonyl and/or phosphoryl oxygens of the phosphonate. Preferably, the divalent metal complex of the phosphonate according to formula (I) is a six-membered chelate ring according to formula (2) and/or (3).

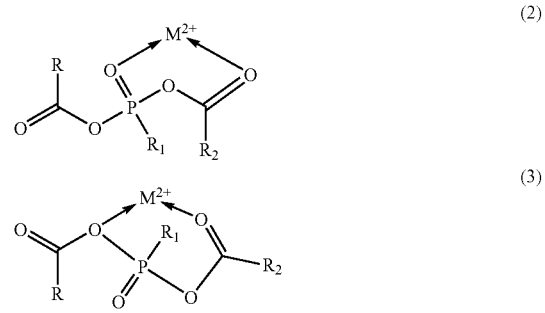

wherein $M^{2+}$ is a divalent metal and R, $R^1$ and $R^2$ are as defined above.

In a preferred embodiment, the divalent metal phosphonate complex is calcium diacetyl hydrogen phosphonate complex, preferably having a structure according to formula (4) and/or (5).

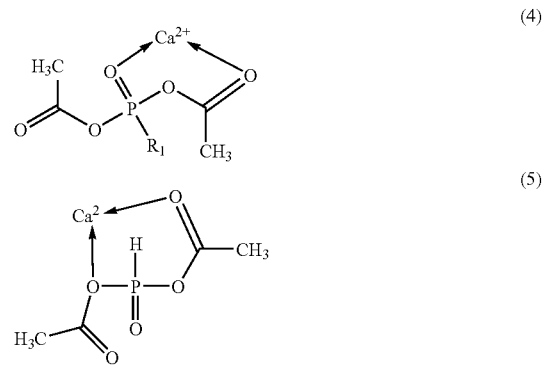

The present inventors have surprisingly found that complexes (4) and (5) allow the ratio of 5/3 and 1.67 respectively between Ca/P to be kept until the precursor decomposes to form hydroxyapatite.

In a fifth aspect, the present invention is directed to a method of preparing a phosphonate compound according to formula (1):

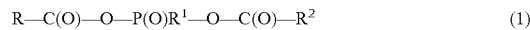

the method including reacting a phosphonate compound according to formula (6)

with an acid $R^5$—C(O)—OH for a time and at a temperature sufficient to effect conversion to the phosphonate (1), wherein R, $R^1$ and $R^2$ are as defined above; and $R^3$, $R^4$ and $R^5$ are selected from the group consisting of hydrogen, substituted alkyl groups and unsubstituted alkyl groups.

Preferably, $R^2$ and $R^4$ are alkyl groups and $R^1$ is hydrogen such that the phosphonate according to formula (6) is a dialkyl hydrogen phosphonate. The diallyl hydrogen phosphonate may be formed in situ from trialkyl phosphite. For example, the present inventors have found that triethylphosphite in the presence of calcium diethoxide and/or calcium acetate and ethylene glycol is able to form diethyl hydrogen phosphonate which is then available for further reaction, More preferably, R, $R^2$ and $R^5$ are methyl groups, $R^1$ is hydrogen and $R^3$ and $R^4$ are ethyl groups, such that the phosphonate according to formula (1) is diacetyl hydrogen phosphonate and the phosphonate according to formula (6) is diethyl hydrogen phosphonate.

Preferably, the method is carried out in the presence of a divalent metal precursor. The presence of a divalent metal precursor allows for direct conversion to the divalent metal phosphonate complex according to the fourth aspect of the invention. The divalent metal may be selected from the group consisting of calcium, magnesium, manganese, strontium, copper and zinc metal. Preferably, the divalent metal is calcium. Examples of suitable divalent metal precursors may include but are not limited to divalent metal salts of carboxylic acids, such as calcium formate, calcium acetate and/or calcium propionate, and/or metal alkoxides such as, calcium methoxide and calcium diethoxide. One or more divalent metal precursors may be employed in the reaction.

The reaction is preferably carried out in a solvent system capable of solubilising the reactants and it will be appreciated that the particular solvent system used will depend on the reactants. Examples of solvents that may be used in the process include but are not limited to glycols such as ethylene glycol, ethanol, methanol or combinations of any or all of these alcohols.

Ethylene glycol, for instance, is effective in solubilising calcium diethoxide or calcium acetate.

The ratio of solvent/acid may range from 4:1 to 1:3. Preferably, the solvent and acid are present in approximately a 1:1 ratio.

It will be appreciated that the temperature required for the reaction will vary depending on the reacting compounds. A lower temperature generally will require a longer reaction time while a higher temperature generally requires a shorter reaction time. The reaction mixture may be heated anywhere between 15° C. and 100° C. At 25° C., conversion has been found to take approximately 1000 h, at 50° C. approximately 192 h and at 70° C. approximately 48 h. Preferably, the reaction mixture is heated at approximately 70° C. Heating may be carried out in an oven or any other suitable heating device.

It may be desirable to carry out the reaction under sealed conditions. This may be desirable, for instance, if one or more of the reactants has a low boiling point. It will be appreciated that this will depend on the reactants and the temperature at which the process is carried out. For example, diethyl hydrogen phosphonate (a phosphonate according to formula (6)) has a low boiling point. Unless the reaction is carried out at a temperature below the boiling point of the solution containing this phosphonate, it is preferable to carry out the process in a sealed vessel.

It may be desirable to carry out the reaction under an inert atmosphere, such as in a dry glove box under nitrogen or argon. This may be desirable, for instance, if moisture and/or oxygen sensitive reactants are used in the reaction. It will be appreciated that this will depend on the reactants. For example, divalent metal alkoxides such as calcium methoxide or diethoxide will normally require an inert atmosphere whereas metal salts such as calcium acetate or formate will not.

The desired Ca/P ratio for the reactants preferably ranges from between 1:1 to about 3:1, more preferably from about 1.5:1 to about 2.5:1, and most preferably the ratio is about 1.67:1. Preferably, the ratio of Ca/P in the reaction mixture is such that a pure monophasic divalent metal phosphate, such as hydroxyapatite, with a precise stoichiometry is obtainable. For instance when the method is directed to preparing diacetyl hydrogen phosphonate and the calcium diacetyl hydrogen phosphonate complex (precursors in the formation of hydroxyapatite) the ratio of Ca/P in the reactants, diethyl hydrogen phosphonate and calcium diethoxide or acetate, is preferably 1.67.

In a preferred embodiment, the fifth aspect of the present invention is directed to a method of preparing a solution or a sol containing diacetyl hydrogen phosphonate, the method including the steps of:
 (i) dissolving calcium diethoxide or acetate in a 1:1 mixture of ethylene glycol and acetic acid;
 (ii) adding a stoichiometric amount (Ca/P ratio 1:67) of diethyl hydrogen phosphonate;
 (iii) heating the solution at about 70° C. for up to 48 h to yield diacetyl hydrogen phosphonate in a closed vial so as to avoid evaporation of diethyl hydrogen phosphonate.

In a sixth aspect, the present invention is directed to a process of forming a divalent metal phosphonate complex according to the fourth aspect of the invention wherein the phosphonate compound according to formula (1) of the invention is heated to a temperature sufficient to allow the divalent metal to coordinate to the carbonyl and/or phosphoryl oxygen to form the divalent metal phosphonate complex.

The divalent metal phosphonate complex according to the fourth aspect of the invention and the phosphonate compound according to formula (1) are as described above.

When the reactants are hygroscopic in nature and/or oxygen sensitive, the process is preferably performed in a moisture and/or oxygen free atmosphere. The process, however, may also be performed under any other conditions which provide an atmosphere conducive to the production of the divalent metal phosphonate complex.

The reaction may be carried out in an inert atmosphere, such as under nitrogen or argon, preferably in a dry glove box under nitrogen.

Preferably, the process is carried out using a solution of the phosphonate compound according to formula (1) prepared according to the fifth aspect of the invention.

The phosphonate compound according to formula (1) is heated at a temperature sufficient to allow coordination of the divalent metal to the carbonyl and/or phosphoryl oxygen to form the divalent metal phosphonate complex. The temperature and time of heating will depend on the specific phosphonate compound according to formula (1). Preferably, the phosphonate compound according to formula (1) is heated between approximately 25° C. and 150° C. for a time of approximately 10 to 1000 h. Heating may be carried out in an oven or any other suitable heating device.

The divalent metal phosphonate complex is preferably obtained as a powder.

In a preferred embodiment, the sixth aspect of the invention is directed to a process for the formation of calcium diacetyl hydrogen phosphonate complex, wherein diacetyl hydrogen phosphonate undergoes heat treatment at approximately 130° C. for approximately 48 h to form solid divalent metal phosphonate complexes according to formula (4) and/or (5) as defined above. Calcium acetate may also be formed in this reaction.

In another embodiment, the sixth aspect of the invention is directed to a process of preparing a solution or sol containing calcium diacetyl hydrogen phosphonate complex, wherein a solution of diacetyl hydrogen phosphonate is heated at about 70° C. for about 48 h in a closed vial so that the formed complexes remain dissolved in the solvent. A lower temperature may be used for a longer period of time.

In a seventh aspect, the present invention is directed to a process of preparing a crystalline monophasic and/or bone-like divalent metal phosphate wherein the divalent metal phosphonate complex according to the fourth aspect of the invention is fired to a temperature sufficient to allow to formation of the crystalline monophasic divalent metal phosphate.

The divalent metal phosphonate complex is fired to form a crystalline monophasic and/or bone-like divalent metal phosphate. The divalent metal phosphate may be in powder form, preferably nanocrystalline powder form. It will be understood that different crystalline monophasic and/or bone-like divalent metal phosphates can be formed depending on the ratio of metal to phosphorous used in the reaction. Examples of solid monophasic and/or bone-like divalent metal phosphates include but are not limited to monophasic and/or bone-like hydroxyapatite and other pure calcium phosphates such as tri-calcium phosphates (TCP).

It will be understood that monophasic hydroxyapatite is hydroxyapatite ($Ca_{10}(PO_4)_6(OH)_2$) that consists essentially of calcium atoms, phosphate groups and hydroxy groups. Bone-like hydroxyapatite is not considered to be pure hydroxyapatite and consists of hydroxyapatite and other compounds in which a carbonate group replaces some or all of the hydroxy and phosphate groups in hydroxyapatite. It will be understood that two types of carbonate substitution are possible: A-type and B-type carbonate substitution. A-type carbonate substitution occurs when carbonate replaces one or more hydroxy groups while B-type carbonate substitution occurs when carbonate replaces one or more phosphate groups.

The divalent metal phosphonate complex is fired to a temperature sufficient to allow formation of a crystalline monophasic divalent metal phosphate. The temperature and time of heating will depend on the specific divalent metal phosphonate complex. The divalent metal phosphonate complex may be heated between approximately 200° C. and 1500° C. for a time of approximately 0.1 to 1000 h. The divalent metal phosphonate complex is preferably heated between approximately 500° C. and 800° C. for a time of approximately 2 h. The time of firing may be shorter or longer. The time and temperature will reflect the morphology, the crystal size and the type of carbonate substitution, that is A or B-type carbonate substitution. At lower temperatures, for example 500-800° C. for up to 8 h, the substitution is mainly B-type, that is bone-like, while at higher temperatures, for example 800° C. and higher, the substitution is mostly A-type which is not typical for the bones and other hard tissues. Lower temperatures are preferably due to B-type substitution and because the crystals are small (nanocrystalline) and plate-like (ie the same as the skeleton). Heating may be carried out in an oven or any other suitable heating device.

Preferably, the divalent metal phosphonate complex is prepared according to the sixth aspect of the invention.

In a preferred embodiment, the seventh aspect of the invention is directed to the formation of monophasic or bone-like hydroxyapatite, wherein a calcium complex of diacetyl hydrogen phosphonate is fired at anywhere between approximately 500-800° C. for approximately 2 h to produce crystalline monophasic hydroxyapatite.

The seventh aspect of the invention provides a reliable method of forming divalent metal phosphates such as hydroxyapatite, tri-calcium phosphate and other calcium phosphates under room atmosphere conditions. This makes such divalent metal phosphates more readily available for industrial, chemical, pharmaceutical and medical applications.

Divalent metal phosphates, preferably in powder, more preferably in nanocrystalline powder form, may be shaped and sintered to form sintered monolithic ceramic products which may be used in industrial, chemical and pharmaceutical applications. Nanocrystalline powders may also be used for various industrial, chemical, pharmaceutical and medical applications.

In an eighth aspect, the present invention is directed to a method of forming a sintered monolithic product, the method comprising shaping and sintering one or more divalent metal phosphates prepared according to the seventh aspect of the invention.

The sintered monolithic product may contain one or more different divalent metal phosphates. For instance, they may contain one or more of hydroxyapatite, tri-calcium phosphate and other calcium phosphates. Various pharmaceuticals may also be incorporated into the products to allow slow drug release to the relevant body part(s).

In a ninth aspect, the present invention is directed to a prosthetic implant formed from sintered monolithic ceramic products prepared according to the eighth aspect of the invention. In this aspect, the prosthetic implant can be a dental implant, or an orthopaedic implant, such as a joint replacement, a craniofacial implant, or an ocular implant.

As the present invention is particularly valuable for producing divalent metal phosphates, such as hydroxyapatite, for the manufacture of prosthetic implants, one further step, itself in the form of a process, may be added to the process to improve the strength of the implant, as well as its ability to promote better tissue integration. Two processes for coating an object according to the present invention are described below in the tenth and eleventh aspects.

In a tenth aspect, the present invention is directed to a process for coating an object with a divalent metal phosphate, the process comprising the steps of:
  (a) preparing a sol containing the divalent metal phosphonate complex according to the fourth aspect of the invention;
  (b) dipping the object into the sol;
  (c) heating the dipped object in order to remove any solvent; and
  (d) firing the heated object to allow conversion of the divalent metal phosphonate complex into the divalent metal phosphate.

The object to be coated with the divalent metal phosphate may be the hydroxyapatite object formed following the process according to the first aspect of the invention or any other object formed of any other metallic, ceramic or composite appropriate material, including, but not limited to any metallic material such as titanium and its alloys, cobalt, chromium, molybdenum and relevant alloys, vitallium alloy, zirconium and its alloys, surgical and other stainless steels, and/or ceramic materials such as alumina ($Al_2O_3$), zirconia (PSZ), silicon nitride ($Si_3N_4$), sialons and bioglasses.

When the reactants are hygroscopic in nature, sol preparation is most preferably performed in a moisture free atmosphere. The process, however, may also be performed under any other conditions which provide an atmosphere conducive to the production of the desired solution.

Preferably, the divalent metal phosphonate complex is prepared according to the sixth aspect of the invention.

Preferably, the divalent metal phosphonate complex is calcium diacetyl hydrogen phosphonate complex.

Having prepared a sol containing the divalent metal phosphonate complex the object is then dipped into the solution. The entire object may be submerged in the sol during this dipping step or one or more portions of the object may be dipped into the solution. It is preferred that the dipping takes place in a dry atmosphere, such as in an atmosphere provided by a dry box, however, other alternative or additional atmospheric conditions may also be used.

In step (c), the object, having now been dipped in the sol, is then heated for the purpose of removing any solvent by evaporation. It will be appreciated that the temperature and duration of heating will depend on the solvent to be removed. Heating preferably occurs in an oven or other heating apparatus, and may be performed at a temperature of between about 20° C. and about 200° C., preferably between 50° C. and 150° C., more preferably heating occurs at about 130° C. The object is heated for anywhere between about 1 hour and several days, more preferably between about 16 hours and about 32 hours, and most preferably for about 24 hours, and/or until removal of the solvent and the object is dry. Upon heating, the divalent metal phosphonate complex may solidify.

Preferably, a coating of between 20 nm and 2000 nm preferably approximately 100 nm, is directly applied to the object being coated, such as a coralline hydroxyapatite article. It will be appreciated that the thickness of the coating will depend on the concentration of the solvents used and/or the number of the applied coatings. More preferably, the coating covers the meso and nano-pores within the intra pore trabeculae material being coated, such as a hydroxyapatite article, whilst maintaining the useful large pores.

The coating may also be applied in macro and micro textured (with beads or mesh) and smooth orthopaedic implants such as hip, knee and shoulder implants.

In step (d), the object is fired to allow conversion of the divalent metal phosphonate complex into the divalent metal phosphate. This may ta place at a temperature of anywhere between about 200° C. and about 1500° C., preferably between approximately 500° C. and 1200° C. More preferably, 500-800° C. for a time of approximately 0.1 to 1000 h, preferably approximately 2 h. Preferably, the divalent metal phosphate is formed according to the seventh aspect of the invention.

The preferred result is an object having a portion, a plurality of portions, or its entire body coated with the divalent metal phosphate. Naturally, where variations in the values for the different compounds, atmospheric conditions, etc., have been used, the coating may have a different composition.

In a preferred embodiment, the tenth aspect of the invention is directed to a process for coating an object made of hydroxyapatite material prepared according to the first aspect of the invention, with monophasic bioactive hydroxyapatite, the process comprising the steps of:
  (a) preparing a sol containing calcium diacetyl hydrogen phosphonate complex according to the sixth aspect of the invention;
  (b) dipping the object into the sol;
  (c) heating the dipped object to about 130° C., and
  (d) firing the heated object to between about 500-800° C. to allow conversion of calcium diacetyl hydrogen phosphonate complex into hydroxyapatite.

In an eleventh aspect, the present invention consists in a process for coating an object with hydroxyapatite, the process comprising the steps of:
  (a) preparing a sol containing a precursor of hydroxyapatite;
  (b) dipping the object into the sol;
  (c) heating the dipped object in order to hydrolyse the precursor of hydroxyapatite; and
  (d) firing the heated object.

As indicated above the selected object for coating with hydroxyapatite may, itself, be the hydroxyapatite object formed following the process according to the first aspect of the invention, the object selected for such coating may equally be any other object formed of any other metallic, ceramic or composite appropriate material, including, but not limited to any metallic material such as titanium and its alloys, cobalt, chromium, molybdenum and relevant alloys, vitallium alloy, zirconium and its alloys, surgical and other stainless steels, and/or ceramic materials such as alumina ($Al_2O_3$), zirconia (PSZ), silicon nitride ($Si_3N_4$), sialons and bioglasses are a few examples of the types of materials which can be coated with hydroxyapatite according to preferred embodiments of the second aspect of the invention.

The sol containing a precursor of hydroxyapatite may be prepared by reacting calcium diethoxide with diethyl phosphite ($HOP(OEt)_2$). In an alternative embodiment, other reactants which provide a sol containing such a precursor of hydroxyapatite may also be used. For example, in a further embodiment the sol may be prepared by reacting calcium acetate with diethyl phosphite.

It may be desirable to carry out the reaction under an inert atmosphere, such as in a dry glove box under nitrogen or argon. This may be desirable, for instance, if moisture and/or oxygen sensitive reactants are used in the reaction. It will be appreciated that this will depend on the reactants. For example, divalent metal alkoxides such as calcium methoxide or diethoxide will require an inert atmosphere. Preparation can also be performed under any other conditions which provide an atmosphere conducive to the production of the desired solution.

While it is preferred that the calcium diethoxide has a high purity, such as that of the compound obtainable from Kojundo Chemical Lab (Saitama, Japan), calcium diethoxide with different levels of purity may also be used. In the most preferred embodiment, prior to being reacted with the diethyl phosphite, the calcium diethoxide is dissolved with the aid of a magnetic stirrer in an appropriate solvent such as, for example, a solution of ethanol, methanol, ethylene glycol or a combination of any or all of these alcohols. In other preferred embodiments, however, stirrers other than magnetic stirrers, are used to dissolve the calcium diethoxide in the ethanol. Proportionately, the amount of calcium diethoxide used can range from anywhere between about 10 mg to about 200 mg, more preferably from about 50 mg to about 150 mg, and most preferably about 100 mg is used. (It is relevant to use the word "proportionately", as where significantly greater or lesser quantities are required for the respective size of the material being coated, the amount used will clearly need to be apportioned appropriately. Naturally, as already disclosed above in respect of other steps/components of the invention, this equally applies to all of the quantities provided throughout the specification.)

Where about 100 mg of calcium diethoxide has been dissolved, it is preferable that about 1 mg to about 100 mg, more preferably about 30 mg to about 80 mg, and most preferably about 61 mg of diethyl phosphite is added to the solution containing the dissolved calcium diethoxide. In the most preferred embodiment, diethyl phosphite, such as that obtained from the Sigma Chemical Co., St Louis, USA is used. Naturally, other preferred embodiments disclose that diethyl phosphite obtained from other sources can also be used.

In one embodiment, these compounds are reacted by the dropwise addition of the diethyl phosphite to the calcium diethoxide. It is preferable for the addition to be dropwise so that the Ca/P molar ratio of the reactant can be monitored and controlled. The desired Ca/P ratio for the reactant preferably ranges from between about 1:1 to about 3:1, more preferably from about 1.5:1 to about 2.5;1, and most preferably the ratio is about 1.67:1. In an alternative embodiment, the diethyl phosphite and calcium diethoxide are reacted by one other or a plurality of other techniques, which are different to the dropwise addition of one into the other.

Once the reactant contains the desired Ca/P ratio, prior to dipping the object, the reactant is stirred from anywhere between about 30 minutes and several days, and most preferably from between about 1 hour and about 24 hours. Furthermore, the stirring preferably takes place in a dry atmosphere at ambient temperature. However, if other different conditions for the atmosphere are deemed appropriate for the desired outcome, the stirring could equally be performed in an atmosphere having such different conditions.

In a further embodiment wherein the sol is prepared by reacting calcium acetate with diethyl phosphite, the calcium acetate is dissolved in a glycol, preferably ethylene glycol and acetic acid subsequently added to the dissolved mixture. The ratio of ethylene glycol/acetic acid may range from 4:1 to 1:3, preferably 1:1.

Having prepared a sol containing a precursor of hydroxyapatite, step (b) discloses that the object is then dipped into the solution. While in most cases, it is preferred that the entire object is submerged in the sol during this dipping step, in some cases, it may be preferable to coat one or a plurality of portions of the object with hydroxyapatite and therefore only necessary to dip those particular portions of the object into the solution. Once again, it is preferred that the dipping takes place in a dry atmosphere, such as in an atmosphere provided by a dry box, however, other alternative or additional atmospheric conditions may also be used.

In step (c) the object, having now been dipped in the sol, is then heated for the purpose of hydrolysing the precursor of hydroxyapatite. Such heating preferably occurs in an oven or other heating apparatus, and is performed at a temperature of between about 20° C. and about 200° C., more preferably between about 50° C. and about 120° C., and most preferably at about 70° C. The object is heated for anywhere between about 1 hour and several days, more preferably between about 16 hours and about 32 hours, and most preferably for about 24 hours, and/or until the object is dry.

In a preferred embodiment of step (d) the invention, the dried object is then fired at a temperature of anywhere between about 400° C. and about 1500° C., more preferably between about 800° C. and about 1200° C., and most preferably at about 1000° C.

The preferred result is an object having a portion, a plurality of portions, or its entire body coated with monophasic bioactive hydroxyapatite. Naturally, where variations in the values for the different compounds, atmospheric conditions, etc., have been used, the coating may have a different composition.

In a preferred embodiment, the eleventh aspect of the invention is directed to a process for coating an object made of a hydroxyapatite materiel prepared according to the first aspect of the invention, with hydroxyapatite, the process comprising the steps of:
  (a) preparing a sol containing a precursor of hydroxyapatite by reacting calcium diethoxide with diethyl phosphite in glycol under an inert atmosphere in an amount sufficient to achieve a Ca/P ratio of about 1.67;
  (b) dipping the object into the sol;
  (c) heating the dipped object to a temperature of about 70° C. for a period of about 24 hours in order to hydrolyse the precursor of hydroxyapatite; and
  (d) filing the heated object to a temperature of about 1000° C.

In some cases, it may be desirable to form crystalline hydroxyapatite, preferably a nanocrystalline powder, instead of coating an object with hydroxyapatite according to the eleventh aspect of the invention.

In a twelfth aspect, therefore, the present invention is directed to a process for forming crystalline hydroxyapatite, the process comprising the steps of:
  (a) preparing a sol containing a precursor of hydroxyapatite;
  (b) heating the sol in order to hydrolyze the precursor of hydroxyapatite;
  (c) firing the product obtained from step (b) to a temperature sufficient to form crystalline hydroxyapatite.

It will be appreciated that the process steps (a), (c) and (d) in the eleventh aspect of the invention are applicable to above steps (a), (b) and (c) respectively.

Preferably, hydroxyapatite powder, preferably nanocrystalline powder, is formed.

The crystalline hydroxyapatite obtained from the twelfth aspect of the invention may be shaped and sintered to form monolithic sintered products which may be used for industrial, chemical and pharmaceutical applications.

In a thirteenth aspect, the present invention is directed to a method of forming a sintered monolithic product, the method comprising shaping and sintering crystalline hydroxyapatite prepared according to the twelfth aspect of the invention.

The sintered monolithic product may further include one or more different divalent metal phosphates such as tricalcium phosphate and other calcium phosphates. Various pharmaceuticals may also be incorporated into the products to allow slow drug release to the relevant body part(s).

In a fourteenth aspect, the present invention is directed to a prosthetic implant formed from sintered monolithic ceramic products according to the thirteenth aspect of the invention. In this aspect, the prosthetic implant can be a dental implant, or an orthopaedic implant, such as a joint replacement, a craniofacial implant, or an ocular implant.

In preferred embodiments of the tenth and eleventh aspects of the invention, the above techniques for coating a hydroxyapatite material, involve a two-stage application route where in the first stage complete conversion of coral to pure HAp is achieved. In the second stage a sol-gel derived HAp coating (about 100 nm) is directly applied to cover the meso and nano-pores within the intra pore trabeculae material, whilst maintaining the useful large pores.

In preliminary studies, biaxial strength was improved by 100-120% due to this unique double treatment. Additionally, 3-point flexure tests show a 25% increase in flexure strength between hydrothermally converted coral and hydrothermally converted coral samples that have been coated according to the process described in the tenth and eleventh aspects of the invention. This application results in high purity, enhanced durability and strength in the physiological environment through vastly reduced dissolution rates and elimination of intra-trabecular nano and meso-pores.

Materials produced by this double treatment method are advantageous where high strength requirements are pertinent. Current bone graft materials are mainly produced from coralline hydroxyapatite (HAp). Due to the nature so of the conversion process, coralline HAp has retained coral or $CaCO_3$ and the structure possesses nanopores within the inter pore trabeculae resulting in high dissolution rates. Under certain conditions these features reduce durability and strength respectively and hence influence longevity and are not utilised where high structural strength are required. The above two-stage technique, a new coral double-conversion technique, overcomes these limitations.

Due to the increased biaxial strength of hydroxyapatite materials prepared according to the double treatment technique of preferred embodiments of the tenth and eleventh aspects of the invention, they may be used in structurally loaded orthopaedic applications, such as impact grafting, in orbital implants and craniofacial and maxillofacial applications.

Bone grafts can be made using coated materials or sintered products made according to the present invention.

In a fifteenth aspect, the present invention is directed to a bone graft material formed from a coated object produced according to the process described in the tenth and eleventh aspects of the invention.

In a sixteenth aspect, the present invention is directed to a bone graft material prepared from a sintered product prepared according to process described in the eighth and thirteenth aspects of the invention.

In bone graft applications, the hydroxyapatite material prepared by the process according to the first aspect of the invention, the coated object prepared by the process according to tenth and eleventh aspects of the invention and the sintered products prepared according to the eighth and thirteenth aspects of the invention can be used alone or incorporated with bone morphogenic proteins (BMP), collagen, growth factors (GF), marrow stromal cells (MSC). It can also be used as scaffolding in soft tissue applications.

BRIEF DESCRIPTION OF THE DRAWINGS

By way of example, preferred embodiments of the invention are described with reference to the accompanying drawings in which:

FIG. 8 shows a comparison of the mechanical properties of Australian coral before hydrothermal conversion, following hydrothermal conversion according to example 1 and following hydrothermal conversion according to example 1 and coating with hydroxyapatite according to the tenth and eleventh aspects of the invention

PREFERRED MODE OF CARRYING OUT THE INVENTION

With specific reference to the first aspect of the invention, one preferred mode of carrying out the process for preparing hydroxyapatite material by means of hydrothermal conversion, includes the following steps:

(a) providing a sample of coral of the genus Goniopora ($CaCO_3$), from the Great Barrier Reef, off the coast of Queensland, Australia; and adapting the sample to the appropriate shape;

(b) applying a series of pre-conversion steps to the sample, the pre-conversion steps including:

(I) treating the sample to remove impurities therefrom with a series of cleansing step, the cleansing steps including:

(i) treating the sample with boiling water (double distilled) for 10 minutes and with an ultrasonic bath for 2 minutes;

(ii) rinsing the sample from (b)(I)(i) with fresh water (double distilled);

(iii) subjecting the sample from (b)(I)(ii) to a repeat of steps (b)(I)(i) and (b)(I)(ii);

(iv) immersing the sample from (b)(I)(iii) in a solution of 5% NaClO for 24 hours;
(v) subjecting the sample from (b)(I)(iv) to a repeat of steps (b)(I)(i) and (b)(I)(ii); and
(vi) drying the sample form (b)(I)(v) at 70° C. for 12 hours; and
(II) heating the sample from (b)(I)(vi) to 300° C. at the heating rate of 5° C./min for 12 hours using a tube furnace; and
(III) washing the heated sample in boiling water, and then drying the heated sample; and
(c) applying a series of hydrothermal conversion steps to the sample, the hydrothermal conversion steps including:
(I) placing the sample from (b)(III) in a Micro Reactor (Parr Instrument Company, USA) with a Teflon liner, and treating that sample with a supersaturated solution of $[(NH_4)_2HPO_4]$ (1M) having a Ca/P mol ratio of 10/20, the treatment being carried out at a temperature of 250° C. and at a pressure of 3.8 MPa for 24 hours; and
(II) washing the sample from (c)(I) by subjecting it to a repeat of steps (b)(I)(i) and (b)(I)(ii), and then drying the sample at 70° C. for 12 hours.

The following example provides a more detailed explanation and analysis of the effects of following these steps on a sample of coral.

EXAMPLE 1

Coralline Hydroxyapatite Preparation

The coral, similar to the genus Goniopora, was obtained from the Australian Great Barrier Reef. The coral, shaped in the form of a block or sphere was treated with boiling water and 5% NaClO solution. The treated coral was placed in a Parr bomb with a Teflon liner together with di-ammonium hydrogen phosphate solution. The hydrothermal process was carried out at 250° C. and 3.8 MPa for 24 hours. The product was then washed and dried.

The samples of the coral, pre-heated and coralline hydroxyapatite were analysed using Fourier transform infrared (FTIR) spectrophotometer, nuclear magnetic resonance (NMR), X-ray diffraction (XRD), and thermogravimetric and differential analysis (TGA/DTA). Scanning electron microscopy (SEM) was used to examine the above samples as supplied.

Results and Discussion

Characterisation of Coral

Figure 1:
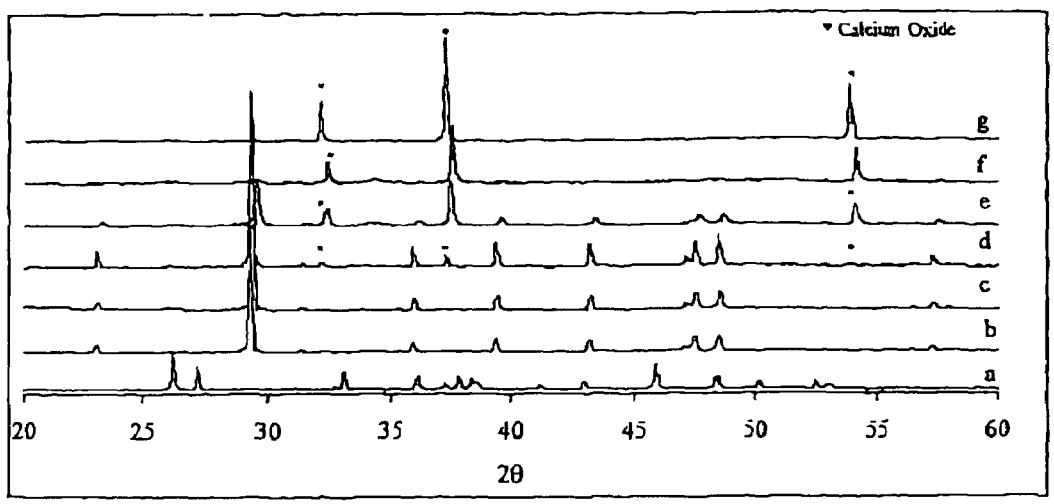
FIG. 1 illustrates the XRD patterns of (a) new species coral, of samples treated in air for 4 hours at (b) 300° C., (c) 500° C., (d) 650° C., (e) 700° C., (f) 800° C. and (g) 900° C., according to example 1.

XRD pattern of untreated coral is shown in FIG. 1a and exhibits aragonite phase of $CaCO_3$ (JCPDS 5-0453). The corals were heated at 300° C., 500° C., 650° C., 800° C. and 900° C. in air for 4 hours, respectively. The resulting products were examined by XRD and the results are shown in FIGS. 1b-g. The XRD patterns of corals heated at 500° C. (FIG. 1c) correspond to the calcite phase of calcium carbonate (JCPDS 5-0586). The diffraction peaks of coral heated to 650° C. (FIG. 1d) show the addition peaks, which are contributed to calcium oxide (JCPDS 37-1497). The more peaks corresponding to calcium oxide are observed and the less peaks to calcium carbonate are found in XRD patterns with increasing in heating temperatures (FIGS. 1e and 1f). The XRD pattern of coral heated to 900° C. (FIG. 1g) shows only presence of calcium oxide.

Thermal analysis of coral exhibited three endothermic peaks at 60, 316 and 751° C., respectively. The first endotherm corresponds to the evolution of adsorbed moisture. The second, accompanied by about a 2% weight loss, may be contributed to by the removal of organic impurities in corals because there was no decomposition of phase observed at this temperature by the examinations of corals using XRD. The third peak, accompanied by a large weight loss (56%), corresponds to the decomposition into calcium oxide from calcium carbonate of coral.

Hydroxyapatite Formation

Figure 2:
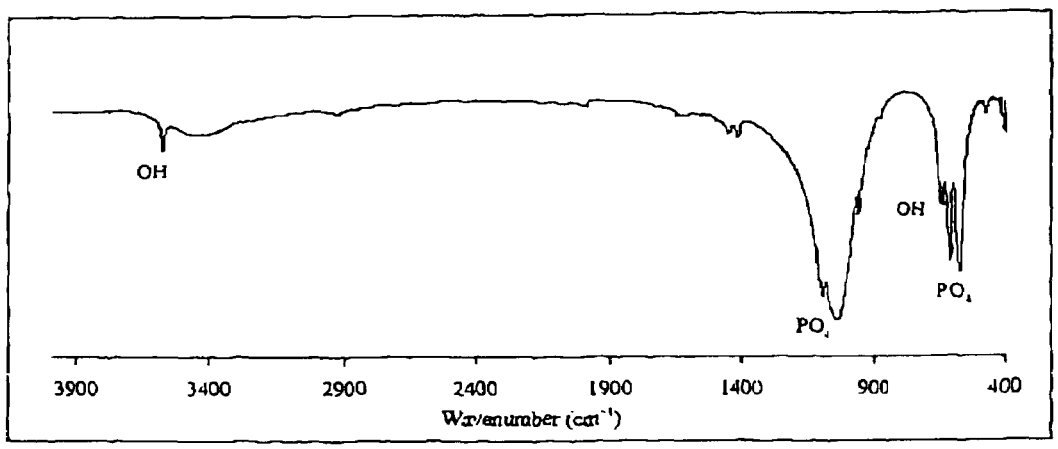
FIG. 2 illustrates the infrared spectrum of a coralline hydroxyapatite according to example 1.

The IR spectra of the converted hydroxyapatite (FIG. 2) showed absorption bands P—O at 1091, 1060 sh, 964, 602, 564 and 476 cm$^{-1}$, and bands indicative of the O—H functional group at 3581 and 636 cm$^{-1}$.

Solid $^{31}$P NMR spectrum of the coralline hydroxyapatite exhibited single one peak at 2.89 ppm relative to 85% $H_3PO_4$ (external reference), indicating conversion to monophasic (or pure) hydroxyapatite.

Figure 3:
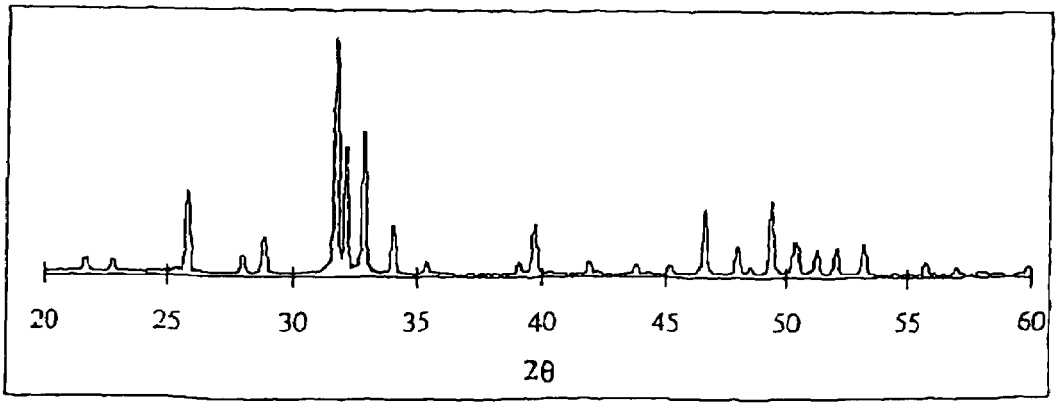
FIG. 3 illustrates the X)RD pattern of a coralline hydroxyapatite, according to example 1.

The products after hydrothermal process were then identified by powder X-ray diffraction to be single phase of hydroxyapatite (JCPDS 9-0432). The XRD pattern of converted hydroxyapatite is shown in FIG. 3 and demonstrates high crystallinity. No peaks corresponding to $CaCO_3$ or CaO were found, suggesting that the conversion was complete.

Morphology of Coralline Hydroxyapatite

The morphology of the coral before and after conversion was studied using SEM. An SEM image of Australian coral after conversion is given in FIG. 4. The pores in the structure were found to increase in size after hydrothermal conversion. Even with increased pore size the interconnecting material is substantial enough to maintain the strength of the coral.

Figure 5:
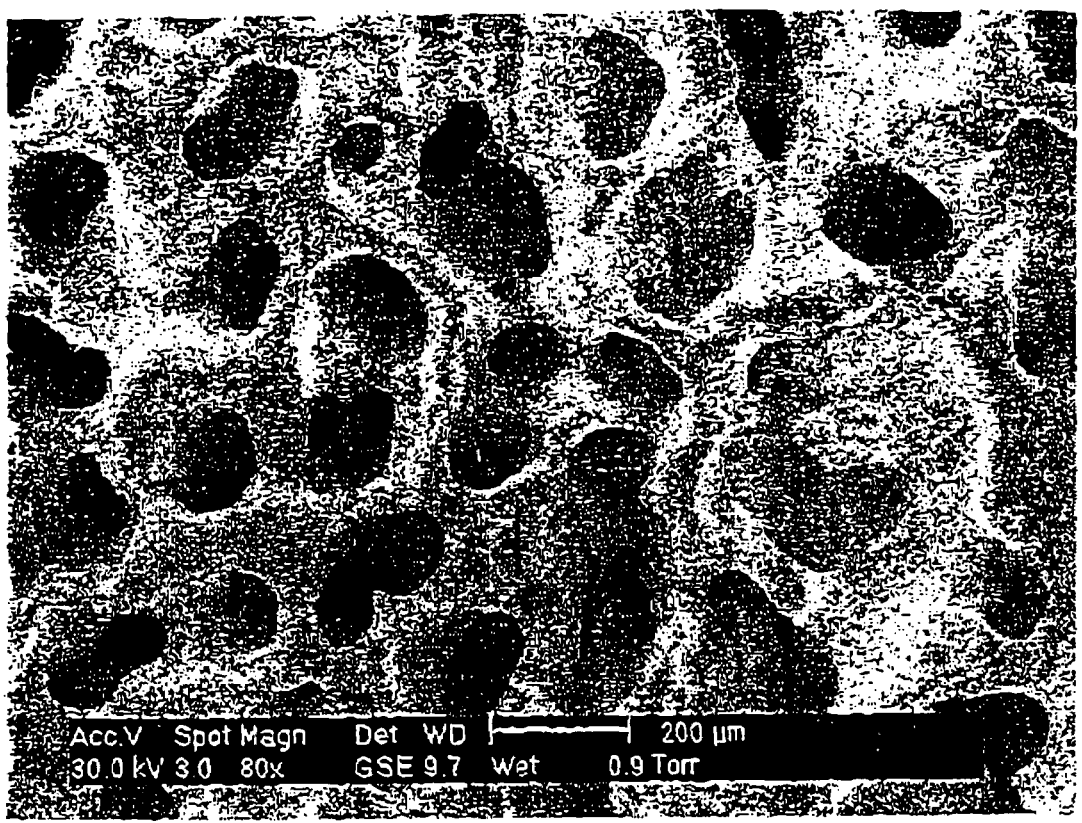
FIG. 5 is an SEM image of a sample of Australian coral following hydrothermal conversion according to example 1.

This example has demonstrated that under a controlled hydrothermal exchange, coralline hydroxyapatite with a porous structure can be produced from Australian coral (see FIG. 5). It has also demonstrated that the conversion to hydroxyapatite can be achieved at relatively low pressure. The hydroxyapatite obtained retains the interconnectivity of coral.

EXAMPLE 2

An 18 mm orbital implant made of hydroxyapatite material was prepared according to the process described in example 1 with 100% conversion from coral to hydroxyapatite.

As explained above, since the present invention is particularly valuable for producing hydroxyapatite for the manufacture of prosthetic implants, one further step, itself in the form of an additional process, may be added to the process to improve the strength of the implant, as well as its ability to promote better tissue integration. The tenth and eleventh aspects of the invention disclose this process.

In accordance with the eleventh aspect, one preferred mode of carrying out the process for coating an object with hydroxyapatite includes the following steps:
(a) preparing a sol containing a precursor of hydroxyapatite, the preparation including carrying out the following steps in a moisture free atmosphere:
(i) with the aid of a magnetic stirrer, dissolving 100 mg of high purity calcium diethoxide (obtained from Kojundo Chemical Lab., Saitama, Japan) in ethanol (obtained from BDH, Kilsyth, Australia); and
(ii) adding 61 mg of diethyl phosphite to the solution from (a)(i) in a dropwise fashion until a Ca/P molar ratio of 1.67:1 is obtained; and stirring the reactant for 24 hours;

(b) dipping the relevant portions of the object (for example, the object formed following the process defined by example 1) into the sol;
(c) heating the dipped object at 70° C.-130° C. in an oven for 24 hours, thereby causing hydrolysis of the precursor of hydroxyapatite; and
(d) firing the heated object at 1000° C. for 2 hours.

Figure 6:
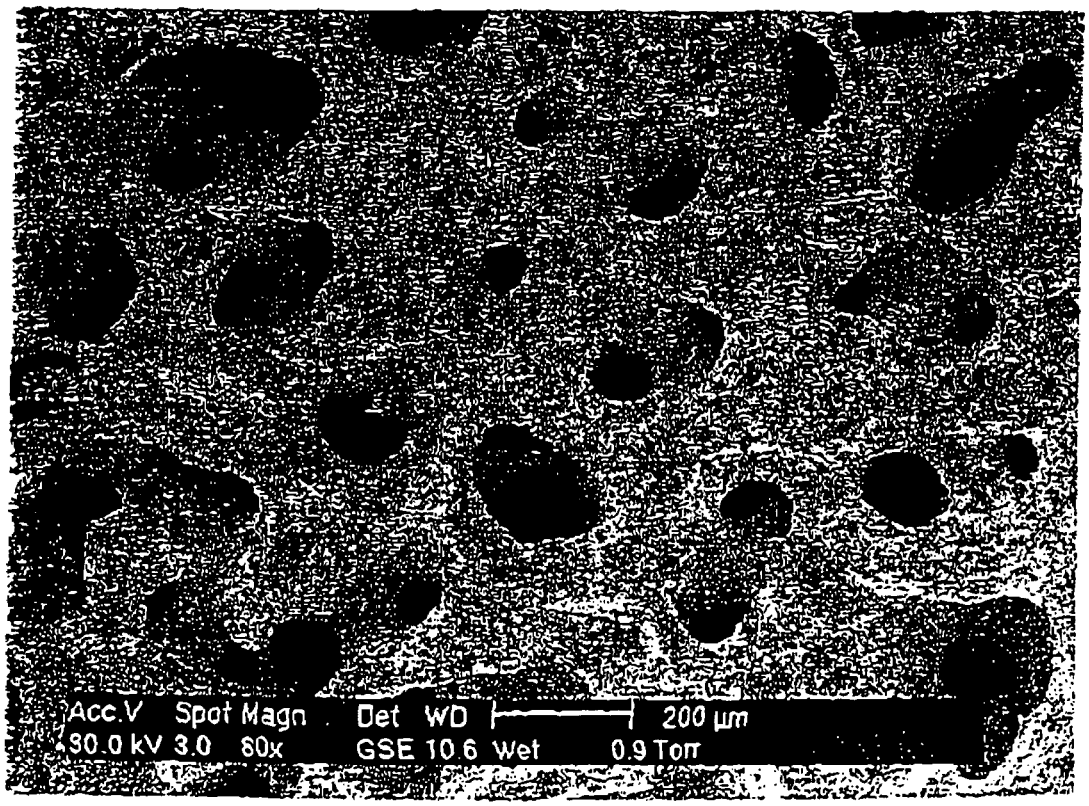
FIG. 6 is an SEM image of a sample of Australian coral following hydrothermal conversion according to example 1 and coating with hydroxyapatite according to the eleventh aspect of the invention.

A comparison of the SEMs from FIGS. 5 and 6 illustrate the structural differences between a sample of Australian coral treated solely with the process according to example 1, and another sample treated with the process according to example 1 as well as the process detailed immediately above (ie the process according to a preferred mode of carrying out the eleventh aspect of the invention).

A further mode of preparing a sol for coating an object with hydroxyapatite includes the following steps:
(a) preparing a sol containing a precursor of hydroxyapatite, the preparation including carrying out the following steps:
  (i) with the aid of a magnetic stirrer dissolving 2 g of calcium acetate $Ca(OAc)_2xH_2O$ in 10 g of ethylene glycol and adding to this mixture 9.6 g of acetic acid;
  (ii) adding 0.938 g of diethyl phosphite $(C_2H_5O)_2 P(O)H$ to the solution of (a)(i); and stirring the reactant for a period of time and preferably at least 30 minutes;
  (iii) maintaining the solution in a closed vial at a temperature of between 50 and 70° C. (at 50° C. for up to 192 h and at 70° C. for up to 48 h so as to allow for ligand substitution to occur) for a period of time and preferably at least 24 hours.
(b) dipping the relevant portions of the object (for example, the object formed following the process defined by example 1) into the sol;
(c) firing the heated object at 700° C.

Figure 7A:
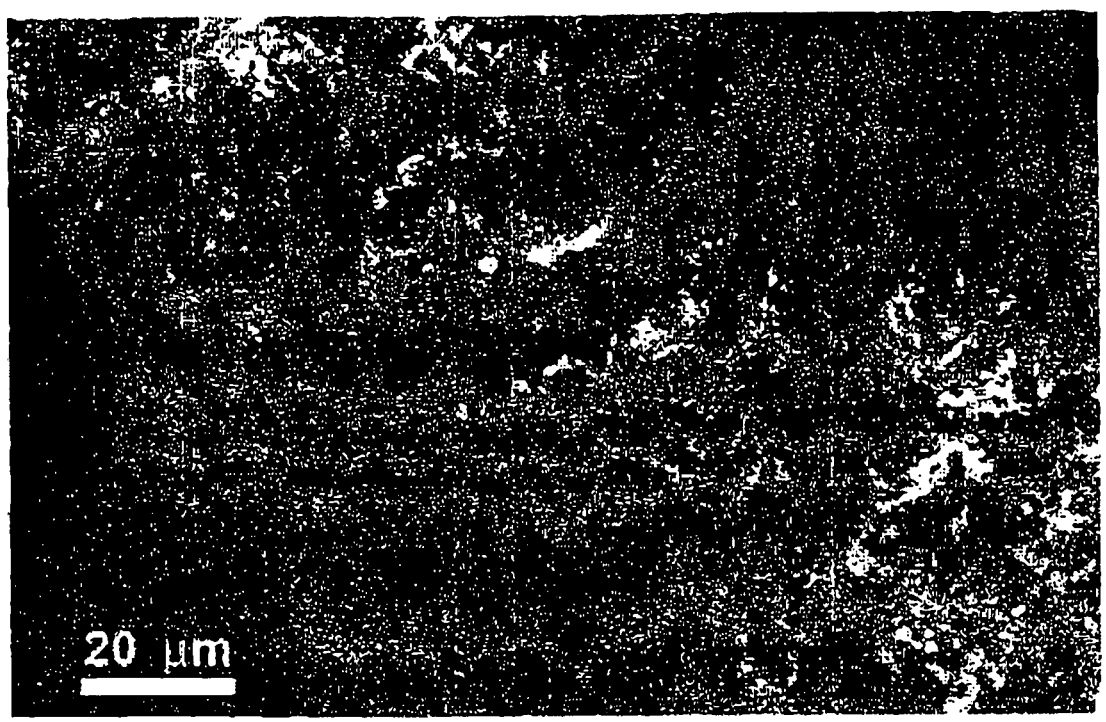
FIGS. 7A, 7B and 7C are SEM images of the connection regions between the pores of Australian coral before hydrothermal conversion (7A), after hydrothermal conversion according to example 1 (7B), and following hydrothermal conversion according to example 1 and coating with hydroxyapatite according the eleventh aspect of the invention. (7C).
Figure 7B:
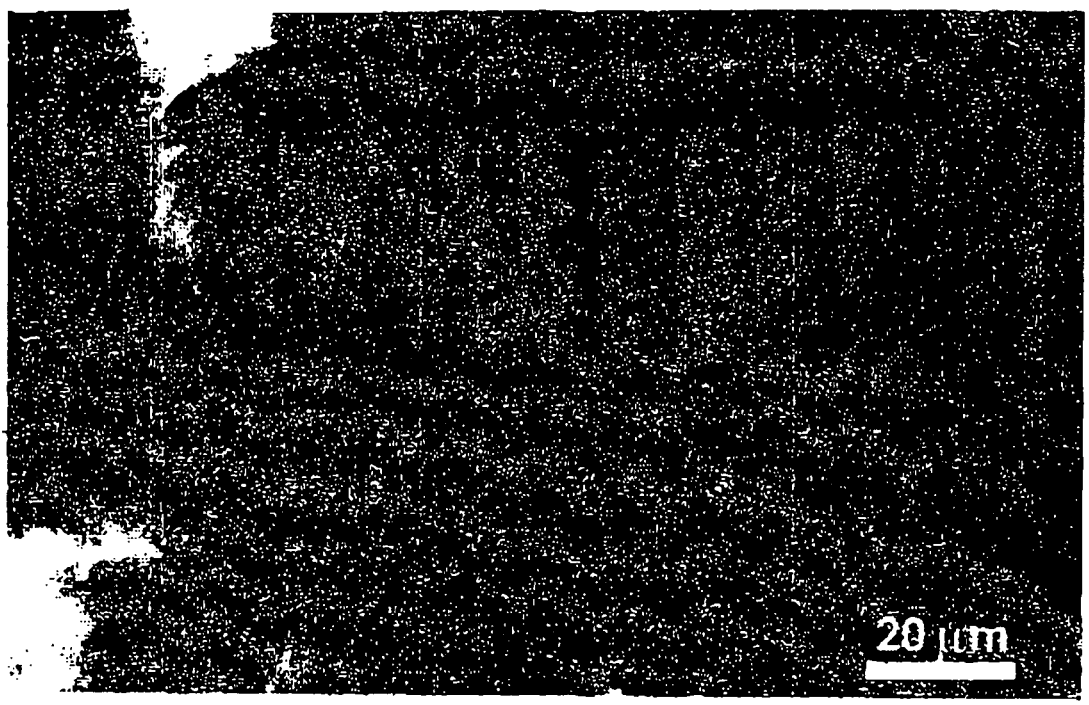
Figure 7C:
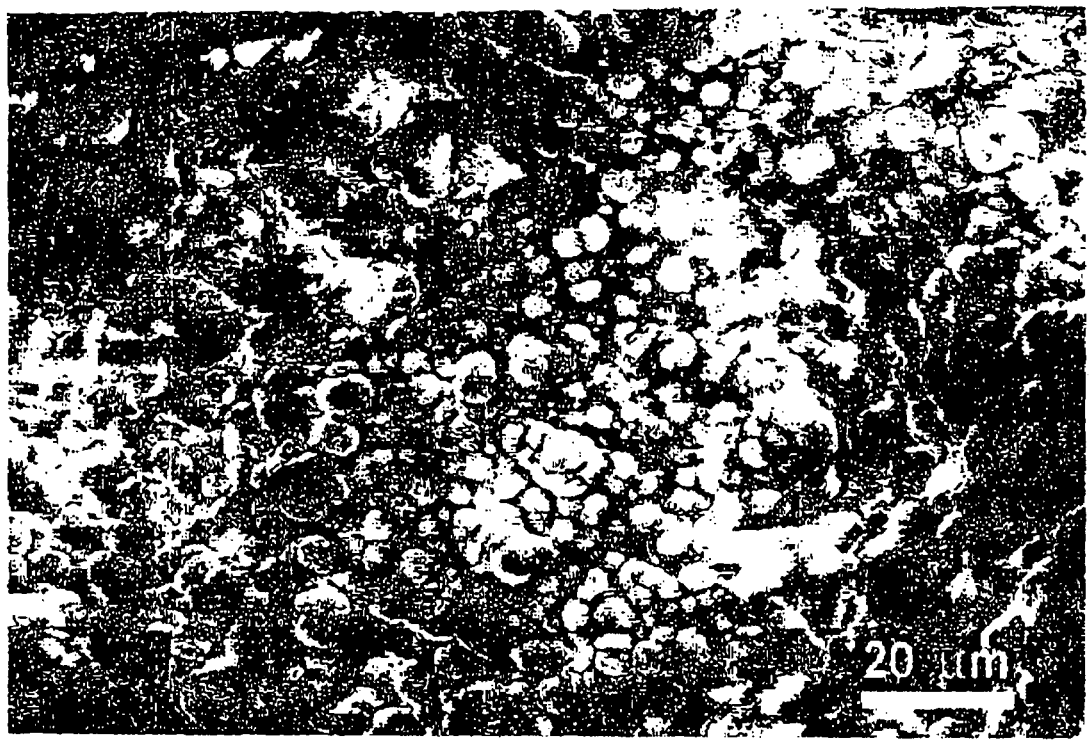

FIGS. 7A, 7B and 7C are SEM images of the connection regions between the pores of Australian coral before hydrothermal conversion (7A), after hydrothermal conversion (7B), and following hydrothermal conversion and coating with hydroxyapatite (7C). From an analysis of these images it was found that the non-converted coral contained meso- and nano-pores within the connecting channels. The hydrothermally converted hydroxyapatite showed a similar microstructure but had a differing chemical composition. The hydrothermally converted and coated coral, however, showed filled meso- and nano-pores and a generally smooth and grainy structure.

FIG. 8 provides a comparison of the mechanical properties of non-converted coral, coral following hydrothermal conversion according to example 1 and coral following hydrothermal conversion according to example 1 and coated with hydroxyapatite according to the process described in the tenth and eleventh aspects of the invention.

The biaxial strength was improved by 120% due to the unique double treatment. This is illustrated in FIG. 8 and summarised below.

|  | Biaxial Strength (MPa) |
| --- | --- |
| Coral | 6.5 ± 2.9 |
| Converted Coral | 7.6 ± 1.4 |
| Converted and Coated Coral | 13.3 ± 6.5 |

Additionally, 3-point flexure tests show a 25% increase in flexure strength between hydrothermally converted coral according to example 1 and hydrothermally converted coral samples that have been coated.

This new application is expected to generate, enhanced durability and strength in the physiological environment through vastly reduced dissolution rates and elimination of intra-trabecular pores.

This new material is suitable for use in prosthetic implants and bone graft applications where high strength requirements and longevity are pertinent.

With specific reference to the third to seventh aspects of the invention, is the following illustrates a preferred mode of forming/prepaying diethyl hydrogen phosphonate, diacetyl hydrogen phosphonate, calcium diacetyl hydrogen phosphonate complex and hydroxyapatite.

Method:

The precursor sol was formed by mixing 0.148 g calcium ethoxide $Ca(OEt)_2$ (Kojundo) or 0.200 g $Ca(OAc)_2xH_2O$ with ethylene glycol (Aldrich) and acetic acid (AnalR) 1:1 mol ratio glycol/acetic acid (1.000 and 0.960 g respectively) in a dry glove box under nitrogen atmosphere (only required when calcium ethoxide is used). A stoichiometric amount (Ca/P ratio 1.67) of diethyl hydrogen-phosphonate 0.094 g $(C_2H_5O)_2P(O)H$ (Sigma) was added after the complete dissolution of calcium precursor. The resulting clear sol was aged at 70° C. up to 48 h in a closed vial. Powders were formed after consequent heat treatment in an oven at 130° C. for 48 h. These powders were fired at temperatures ranging from 200 to 900° C. in order to analyze intermediates, before conversion into hydroxyapatite.

IR: Nicolet Magna IR 560 FT-IR was used for both liquid and solid samples. Spectra of the solids were taken in the 4000-400 $cm^{-1}$ region (64 scans at 4 $cm^{-1}$ resolutions), as 1 mg samples were suspended in 150 mg KBr (16 mm diameter). The chamber was continuously purged during the scanning with purified dry air.

NMR: The characterization of the changes occurring in the initial liquid precursor sol and consequent solid precursor phase was acquired using Bruker DRX-300 300 MHz for protons, and 121 MHz for $^{31}P$, respectively. The sol was analyzed immediately after preparation and after 48 h 70° C. by $^1H$, and $^{31}P$ as the instrument was always operating at 27° C. The chemical shifts for the case of phosphorous NMR were referred to external 85% phosphoric acid while for proton NMR were referred to internal standard—methylene protons of ethylene glycol, present into the system. Two-dimensional (2D) NMR experiment, in particular Correlation Spectroscopy (COSY) for protons was employed to determine the spin-spin coupling between the methylene protons of asymmetrical ester (acquired with spectral window of 3000 Hz, 2048 data points, 512 $t_1$ increments and 2 s relaxation delay). The powders, after drying at 130° C. 48 h, were fired at different temperatures and analyzed by solid-state magic angle spinning (MAS) $^{31}P$ NMR. All solid state NMR experiments were conducted at 5 kHz spinning rate of the probe.

DTA/TG and XRD: Thermal analyses were carried out using a STD 2960 simultaneous analyzer—TA instruments. The powder obtained at 130° C. was heated at 10° C./min to 1000° C. The fired at 700 and 900° C. powders were further analyzed by Siemens D-5000 Diffraktometer, employing CuKα radiation (40 kV, 30 mA). The diffraction pattern was collected over the 2θ ranges 20-60° with acquisition time of 3.0 seconds at 0.02° step size.

Liquid State Reactions (70° C.):

$^1$H NMR (with Calcium Ethoxide as Calcium Precursor)

Figure 9:
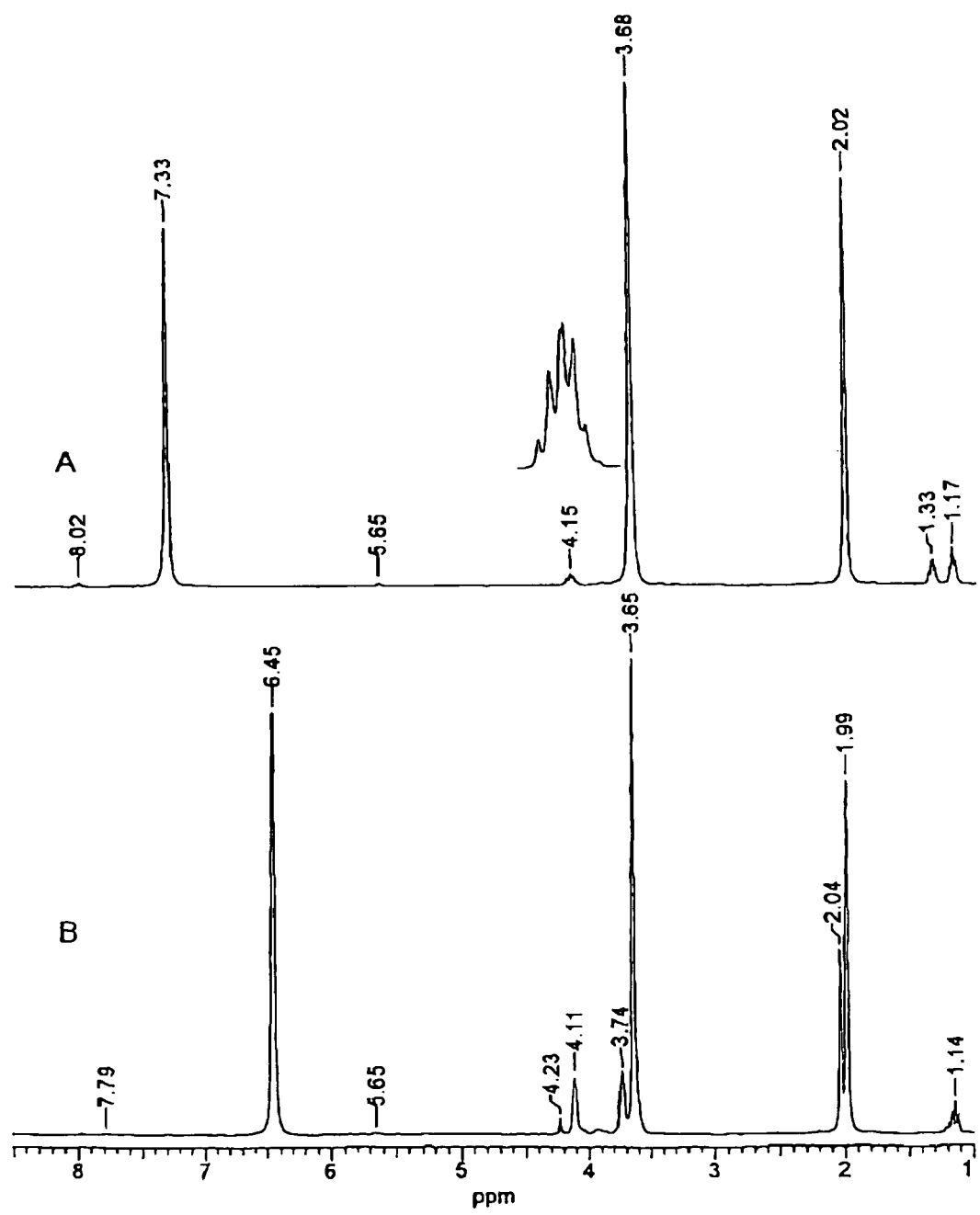
FIG. 9 shows proton NMR spectra of a solution prepared according to a preferred embodiment of the fifth aspect of the invention after A) 30 min of preparation and B) 48 h at 70° C.

The $^1$H NMR spectrum of the initial mixture after 30 min. of preparation is represented in FIG. 9A. The triplets at 1.33 and 1.17 ppm are assigned to the methyl group of diethyl hydrogen-phosphonate and ethoxy groups from calcium ethoxide respectively, while the singlet at 2.02 ppm is assigned to the methyl protons of acetic acid (in the case where calcium acetate is used as the calcium source, the triplet at 1.17 ppm does not exist). The methylene protons of ethylene glycol are represented as a singlet at 3.68 ppm, while the distorted quintet at 4.15 ppm is due to the (—CH$_2$—) of the diethyl hydrogen-phosphonate, which is coupled to both (CH$_3$—) ($^2$J$_{H-H}$=7.0 Hz) of the ethoxy groups and to the phosphorous atom ($^3$J$_{H-H}$=7.5 Hz). The two-dimensional correlation spectroscopic (2D-COSY) NMR data revealed that the methylene protons originating from calcium diethoxide precursor are at 3.7 ppm obscured by the methylene protons of ethylene glycol. The two small singlets at 5.65 and 8.02 ppm (doublet with a spin-spin coupling ($^1$J$_{H-P}$=711 Hz)) are assigned to the proton directly attached to the phosphorous. The peak at 7.33 ppm corresponds to hydroxyl groups of ethylene glycol in solution.

Figure 10:
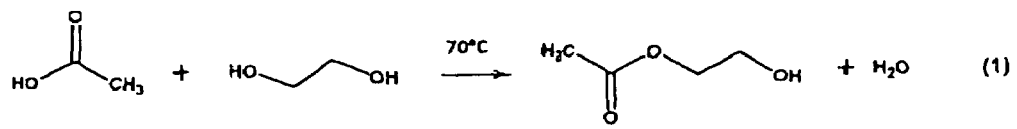
FIG. 10 shows the formation of mono—and diacetyl hydrogen phosphonate according to the fifth aspect of the invention.
Figure 10:
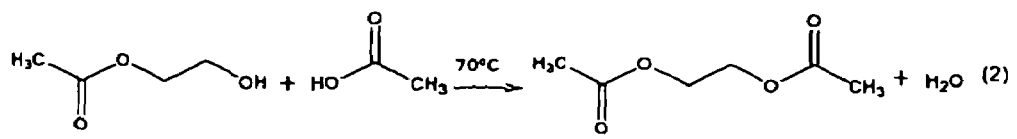
Figure 10:
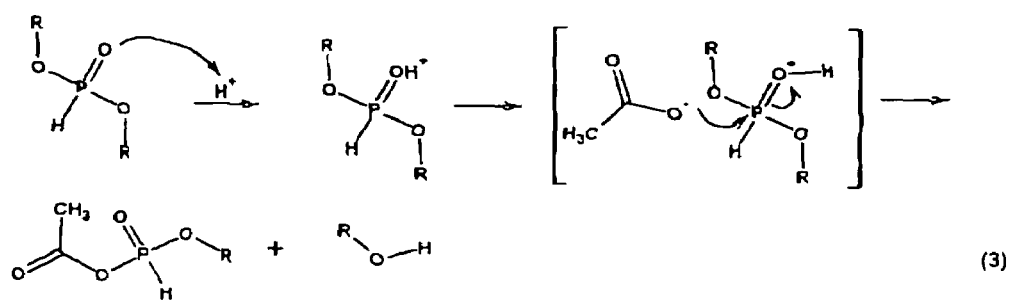
Figure 10:
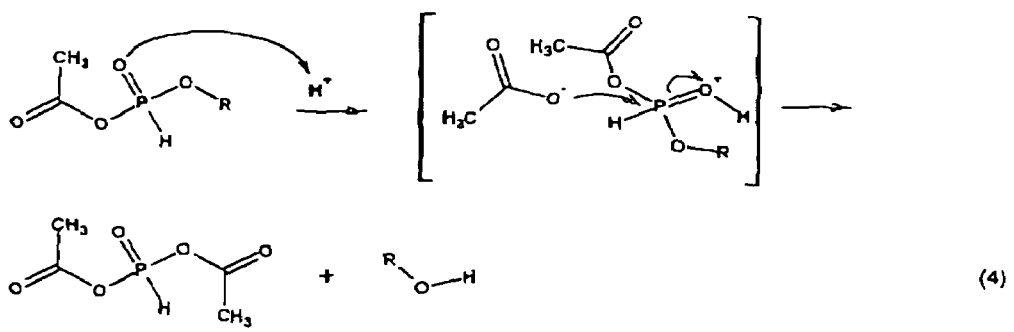
Figure 10:
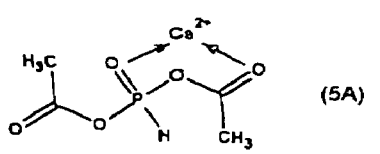
Figure 10:
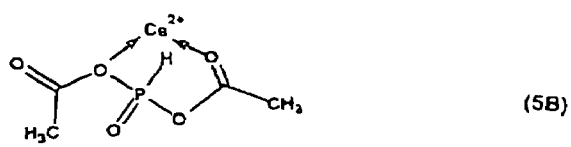

During heat-treatment for 48 h at 70° C. ethylene glycol in the presence of acetic acid undergoes esterification, which was observed and analyzed by $^1$H NMR spectroscopy. The formation of two different types of esters, i.e. asymmetrical glycol monoacetate and symmetrical glycol diacetate has been represented by Equations 1 and 2, respectively (FIG. 10). Two-dimensional (2D) $^1$H NMR experiment, in particular 2D-COSY for protons was employed to determine the spin-spin coupling between the methylene protons of asymmetrical ester.

The new singlet at 2.04 ppm is assigned to methyl protons of both esters (FIG. 9B). The two singlet peaks at 3.74 and 4.11 ppm correspond to the two-methylene groups (—CH$_2$—) of asymmetric glycol mono-acetate ester. The singlet at 4.23 ppm is assigned to (—CH$_2$CH$_2$—) methylene groups of symmetrical glycol diacetate ester. The proton directly attached to phosphorous atom results in two singlets at 5.65 and 7.79 ppm with a spin-spin coupling constant $^1$J$_{P-H}$=642 Hz which is consistent with phosphonate form of phosphorous precursor. The chemical shift of the hydroxyl groups is very sensitive to pH and the polarity of the medium. Therefore, the up-field shift of the peak at 6.45 ppm (assigned to OH) is as a result of water formation during esterification and change of pH due to consumption of acetic acid.

The formation of these two types of esters: glycol monoacetate and glycol diacetate is not crucial for the formation of diacetyl hydrogen phosphonate, they just accompany its formation.

$^{31}$P NMR

In order to provide additional information for the observed reactions, the formation and subsequent reactions of phosphorous species were investigated using $^{31}$P proton coupled NMR in the presence and absence of calcium ions. The $^{31}$P proton coupled NMR spectra for the freshly made solutions displayed almost identical resonances (FIGS. 3A and 4A) at 13.24 and 7.38 ppm ($^1$J$_{P-H}$=712 Hz) and at 12.89 and 7.01 ppm ($^1$J$_{P-H}$=714 Hz) for the solution without and with Ca$^{2+}$ respectively. The large coupling constants in both spectra and the splitting of each arm of the doublets (further spin coupling to the methylene protons form quintets ($^3$J$_{P-H}$=9.25 Hz) revealed that immediately after preparation the phosphorous precursor is in diethyl hydrogen-phosphonate form.

Figures 4A, 4B, 4C:
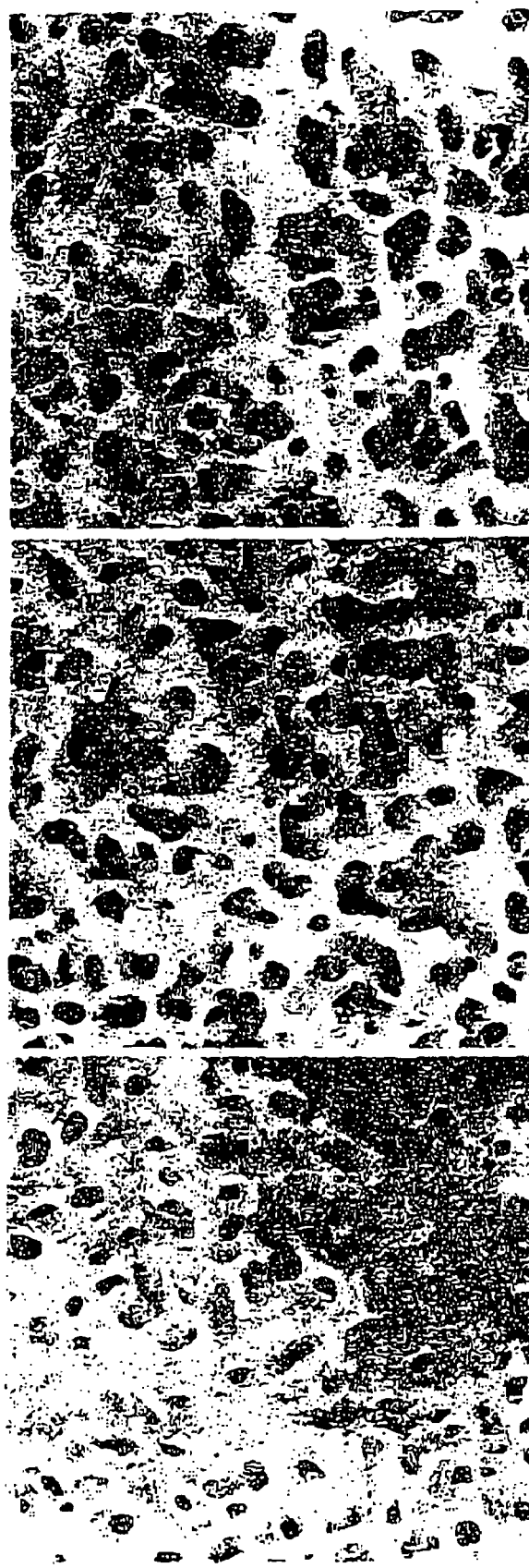
FIGS. 4A-C is a series of SEM images of Australian coral before hydrothermal conversion (4A), heated at 300° C. (4B), and after hydrothermal conversion (4C), according to example 1.

After heat treatment at 70° C. for 48 h, however, the sol without calcium ions has a major doublet at 8.08 and 2.50 ppm $^1$J$_{P-H}$=678 Hz, accompanied with three sets of doublets (minor) peaks at 11.07 and 5.40 ppm ($^1$J$_{P-H}$=689 Hz), 10.19 and 4.56 ppm ($^1$J$_{P-H}$=684 Hz) and 10.42 and 4.76 ppm ($^1$J$_{P-H}$=687 Hz) (FIG. 3B). These downfield signals showed unresolved $^3$J$_{P-H}$ coupling and hence, were assigned to the intermediates that were being converted to diacetyl hydrogen-phosphonate. On the other hand, the sol in the presence of calcium ions shows two minor resonances up field to the main doublet (7.91 and 2.63 ppm $^1$J$_{P-H}$=642 Hz same value obtained by $^1$H NMR) (FIG. 4B). These minor signals at 7.27 and 2.00 ppm ($^1$J$_{P-H}$=640 Hz) and at 6.95 and 1.77 ppm ($^1$J$_{P-H}$=629 Hz) most probably are due to chelation of Ca$^{2+}$ to the mixed anhydride.

$^{31}$P solution NMR gave the most valuable information of the reaction in liquid state. It should be noted that the presence of calcium ions, water and ethylene glycol is not important for the formation of diacetyl hydrogen phosphonate. They accelerate the reaction only. In a separate experiment diacetyl hydrogen phosphonate was obtained via chemical reaction between acetic acid and diethyl hydrogen phosphonate only, but it took longer (96 h at 70° C. compared to 48 h at the same temperature for the "real" solution). Ethylene glycol acts mainly as a solvent of calcium acetate or calcium ethoxide. A calcium source is needed for the complex formation, which after decomposition at around 400° C. gives hydroxyapatite.

Nucleophilic Substitution

Water that is formed in situ (resulting from the esterification reactions) partially ionises the acetic acid to establish equilibrium between protons and acetate ions. These protons interact with the phosphoryl oxygen resulting in an increase electron demand on the phosphorous atom (Eqn. 3 in FIG. 10). Therefore, the formation of number of reaction intermediates is expected as a result of competitive attack on the phosphorous by nucleophiles such as ethylene glycol and acetate ions. In general, the ligand substitution may also be facilitated by metal ion catalysis, where calcium ions act as general acid catalysts, whereby phosphoryl group could be coordinated to the metal and thus increasing susceptibility to nucleophilic attack on phosphorous. Calcium ions can also catalyse the nucleophilic substitution by coordinating with the leaving group. This coordination increases the polarization of phosphorous-ethoxy group bond, and facilitates the departure of the leaving group. Therefore, it may be concluded that both (H$^+$) and calcium ions are able to contribute simultaneously to the ligand substitution process. Reactions between diethyl hydrogen-phosphonate and acetic acid most probably proceed in a one-step process in which the leaving group (ethoxy) is being expelled at the same time of the nucleophilic attack by acetate group. The mixed intermediate: alkoxy-acetyl phosphonate reacts further with another acetate anion resulting in the formation of diacetyl hydrogen-phosphonate (Eqn. 4 in FIG. 10).

Complex Formation

Figure 11:
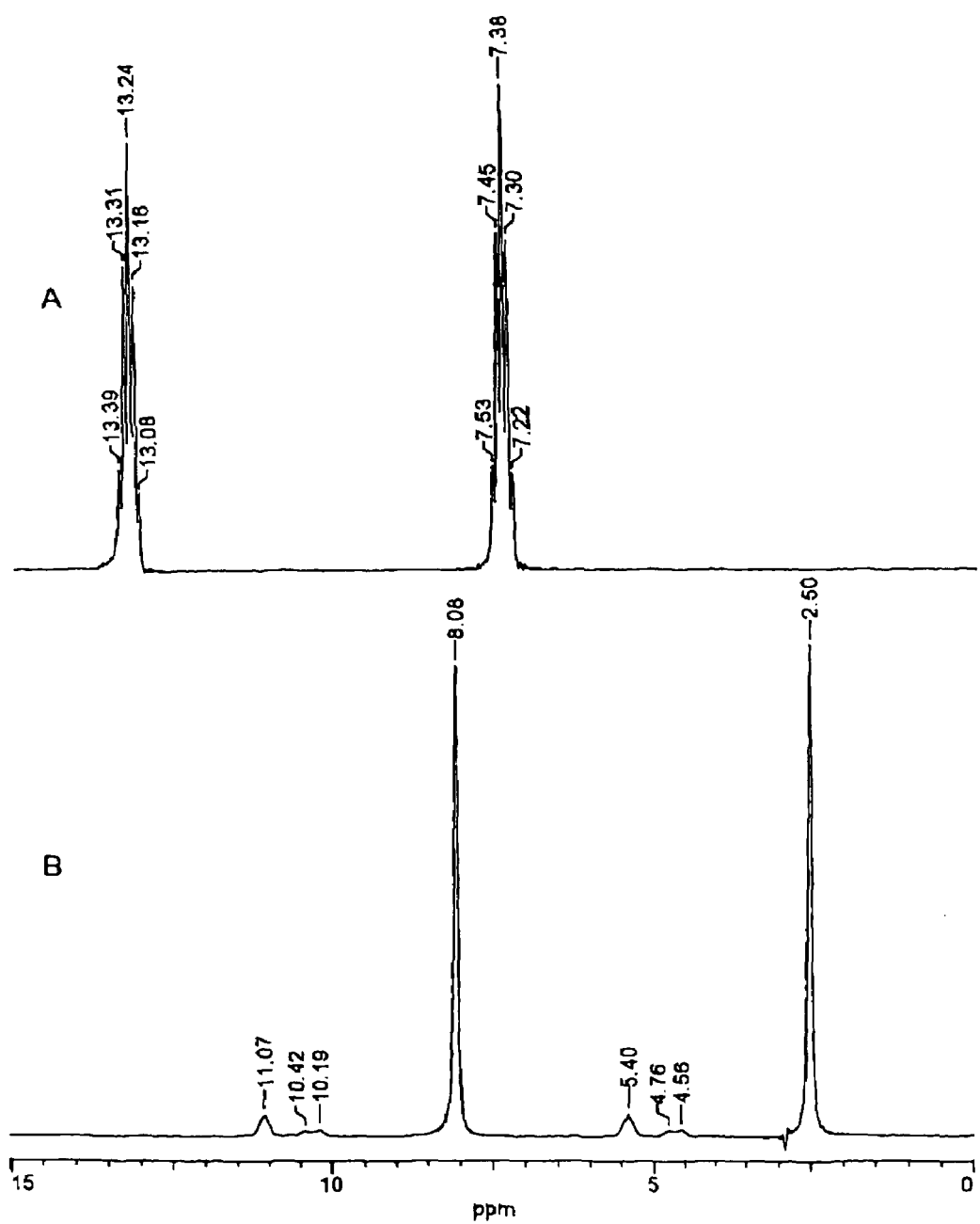
FIG. 11 shows $^{31}P$ proton coupled spectra of the solution according to a preferred embodiment of the fifth, aspect of the invention after A) 30 min of preparation and B) 48 h at 70° C.
Figure 12:
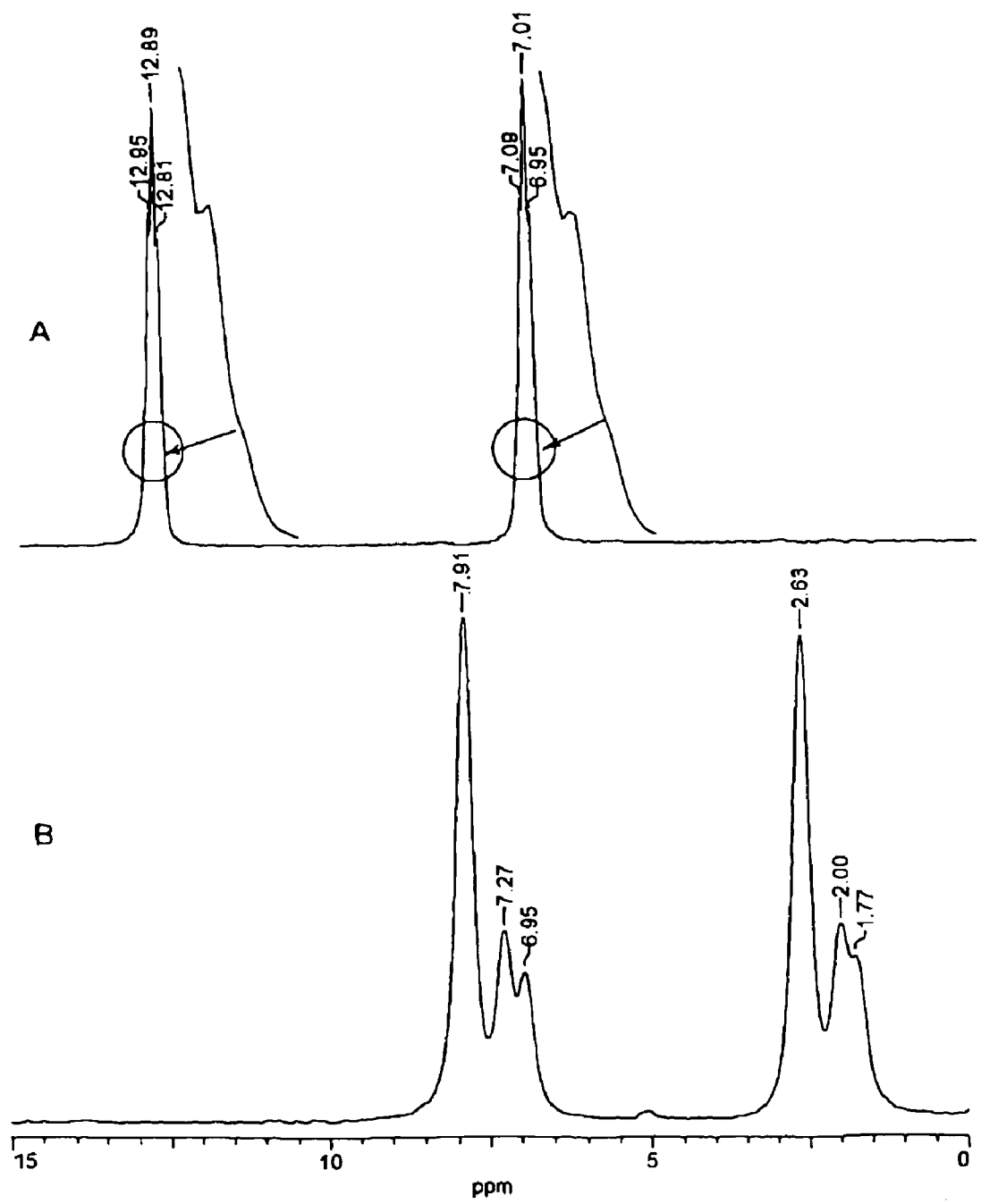
FIG. 12 shows a $^{31}P$ proton coupled spectra of the precursor sol under the same conditions as in FIG. 11 but in presence of calcium ious, A-after 30 min of preparation (arrows show the shoulders of the quintets), B-after 48 h at 70° C.

The diacetyl hydrogen-phosphonate formed in situ will coordinate to calcium ions from the solution giving rise to complexes: chelate rings containing carbonyl and phosphoryl oxygens as six-membered ring appears a priori more probable than other possibilities (Structures 5A and 5B in FIG. 10). Spectroscopic evidence for such chelates was obtained from both liquid and solid state $^{31}$P NMR and from FT-IR spectra of solid complex after drying at 130° C. Another feature is that the major peak in FIG. 11B and all the peaks in FIG. 12B did not reveal any fine structure (no $^3J_{P-H}$ splitting with zero line broadening) suggesting the absence of any long-range (3-bond) spin interactions with the phosphorous. The heterocyclic rings or metal cycles, formed by chelation are similar to other organic ring systems and their stability depends on size, with 6-membered rings being most stable (Structures 5A in FIG. 10). However, it is of interest to note that the metal-ligand complex (Structure 5B) where mixed anhydride oxygen also participate in complex formation owing to reduced, compared to water, effective solvent polarity. In case of a solvent with high polarity this anhydride oxygen can easily be solvated and therefore cannot contribute to complex formation.

The lack of $^3J_{P-H}$ splitting (for this case) indicates that the long range interactions between phosphorous and hydrogen atoms is $^4J_{P-H}$ which strongly supports the suggested fragment of diacetyl hydrogen phosphonate: P—O—C—CH$_3$ Solid State Hydroxyapatite Precursor (130-250° C.):

The FTIR spectra of solid hydroxyapatite precursor samples, heat-treated at 130° C., 200° C. 250° C., 300° C., 500° C., 700° C. and 900° C. identified and confirmed the presence of P—H, P=O, C=O, CO$_3^{2-}$, bonded O—H groups, phosphonate (HPO$_3^2$), aliphatic (CH$_3$— and CH$_2$—) stretches, metal carboxylate functional groups and water molecules existing at respective temperatures.

Aliphatic C-H Stretches (CH$_3$ and CH$_2$)

Figure 13:
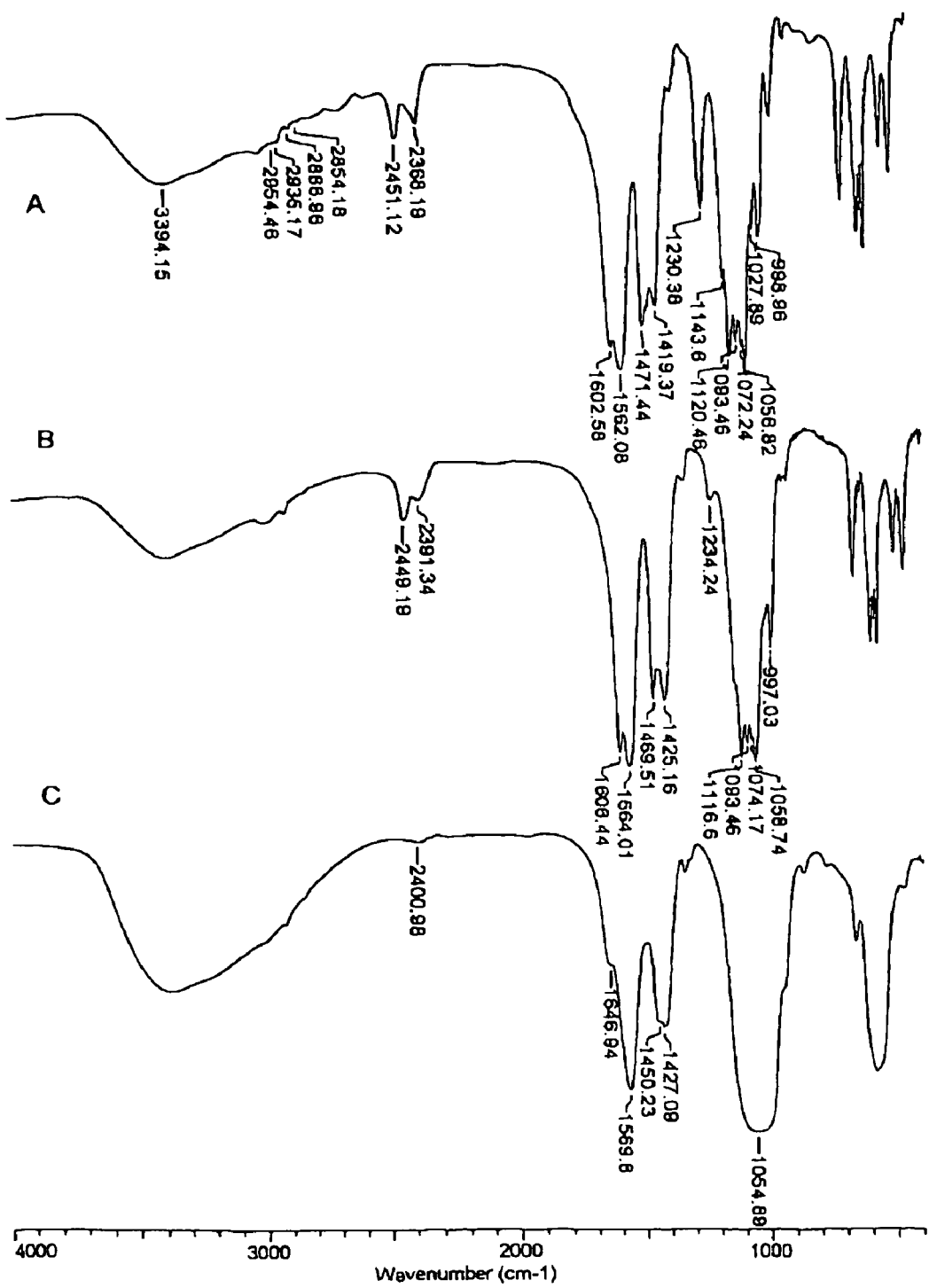
FIG. 13 shows infrared spectra of mixed solid calcium diacetyl hydrogen-phosphonate precursor at: A-130° C. 48 h, B-250° C. 24 h and C-300° C. 24 h. Note the existence of two P—H at 2368 and 2451 $cm^{-1}$ and single P=O at 1230 $cm^{-1}$ vibrations and their decrease with the increase of the temperature.

Peaks at 2954 and 2935 cm$^{-1}$ are assigned to asymmetric methyl and methylene functional groups those at 2887 and 2854 cm$^{-1}$ to symmetric ones, respectively. The C-H stretching bands are seen to be superimposed upon the broad O—H band centered at 3394 cm$^{-1}$ (FIG. 13A). These vibrations exist up to 250° C., which is an evidence of existence and stability of the organic-inorganic solid precursor (FIG. 13B). Fine structures observed on the long-wavelength side of the O—H band represent overtones and combination tones of the functional bands occurring at longer wavelengths.

Phosphonate Stretches PO$_3$H

The IR region between 900 and 1200 cm$^{-1}$ can be used to determine the mode of metal-oxygen-phosphorous bonds. The group of strong intensity bands at 1144, 1120 and 1093 cm$^{-1}$ are assigned to anti-symmetrical stretching modes of PO$_3^{2-}$ ions, and the group with comparable intensity bands at 1072, 1057, 1028, 999 and the shoulder at 991 cm$^{-1}$ are assigned to symmetrical modes (FIG. 13A). The existence of three P—O stretching modes in the region is probably due to the tree phosphonate compounds having different chemical environments since PO$_3$ stretching modes are very sensitive to local asymmetry they are split as a result of the lower symmetry of the phosphonate groups.

Phosphoryl (P—O) and P—H Vibration Modes

The variations of P=O frequencies can be either explained as being indicative of the participation of phosphoryl bond in a complex bond of the type P=O→M$^{n+}$ or indicative of an increase of ionic character of P=O bond. The peak at 1230 cm$^{-1}$ with medium intensity is assigned to these stretches as its intensity decreases with increasing of the temperature. This peak is shifted to lower frequencies compared with pure phosphonate (1256 cm$^{-1}$) suggesting interactions occurring through phosphoryl oxygen.

Neutral phosphonate allyl esters function as unidentate O-ligands, coordinating through the phosphoryl P=O oxygen. When there is a substituent with a potential coordinating site, as in substituted phosphonate esters, it may act as a bidentate chelating agent. The FT-IR spectra of the solid hydroxyapatite precursor show P—H (2451 and 2368 cm$^{-1}$) and P=O signals characteristic of phosphonate structure up to 250° C., 24 h (FIG. 13B). At temperatures of 300° C., 24 h the absence of strong aliphatic, P=O and P—H stretching vibrations indicate that all the phosphonate groups have been ionized forming the very stable orthophosphate anion (PO$_4^{3-}$) (FIG. 13C). The phosphoryl absorption band (P=O) is shifted by $\Delta v=28$ cm$^{-1}$ towards lower wave numbers due to coordination of phosphoryl group to calcium ions.

Carbonyl (C=O) Vibration Modes

The characteristic absorption bands for C=O were split and significantly shifted to lower frequencies (from 1709 to two doublets at $v_{asym}$, 1603, $v_{sym}$, 1471 and at $v_{asym}$, 1562, $v_{sym}$, 1419 cm$^{-1}$). This is an indication of coordination to calcium through C=O group giving rise to an increase of polarization of the bonds (FIGS. 13A and B). The existence of these two sets of doublets in the C=O region, is due to two different ways of bonding between calcium and carboxyl groups. The frequency separation between asymmetrical and symmetrical stretching vibrations ($\Delta v=131$ cm$^{-1}$) and ($\Delta v=144$ cm$^{-1}$) suggests that carboxylate groups act as bidentate ligands, but it is difficult to say whether the acetate groups are chelating (bonded to one) or bridging (bonded to two Ca$^{2+}$ ions).

The calcium ion could be held by bidentate ligand in configuration in which the two functional groups (carbonyl and phosphoryl) are in close proximity, and macro cycle formation will then occur around metal ion. The physical properties of these complexes are markedly different from those of the uncoordinated ligands as calcium can alter the equilibrium position of that system by coordinating with one or more ligands that are components of the equilibrium system. Removal of the metal ion could be possible only by use of vigorous conditions, which also cause degradation of the ligand. Coordination of the diacetyl hydrogen-phosphonate ligand with metal ions can result in polarization of bonds within the ligand, which is a probable explanation for the presence of P—H bond (at 2391 and 2449 cm$^{-1}$ FIG. 13A) up to 250° C., which is otherwise quite labile.

The most important conclusions from FT-EP, data (130-250° C.) are:

- Existence of P—H bond up to 250C for 24 h (if the sample is heated for a lesser period of time, of say approximately 2 h, this P—H bond is readily observable at 300° C.). The existence of this bond supports the hypothesis of the stability of the calcium diacetyl hydrogen phosphonate.
- The existence of P=O vibrations of the solid calcium diacetyl hydrogen phosphonate supports the suggested structure 5B in FIG. 10
- The significant shift (from 1709 of the initial acetic acid to lower frequencies 1603 and lower) and its splitting supports the proposed interactions between calcium ions and carbonyl (C=O) group from diacetyl hydrogen phosphonate.

$^{31}$P Solid State NMR

Figure 14:
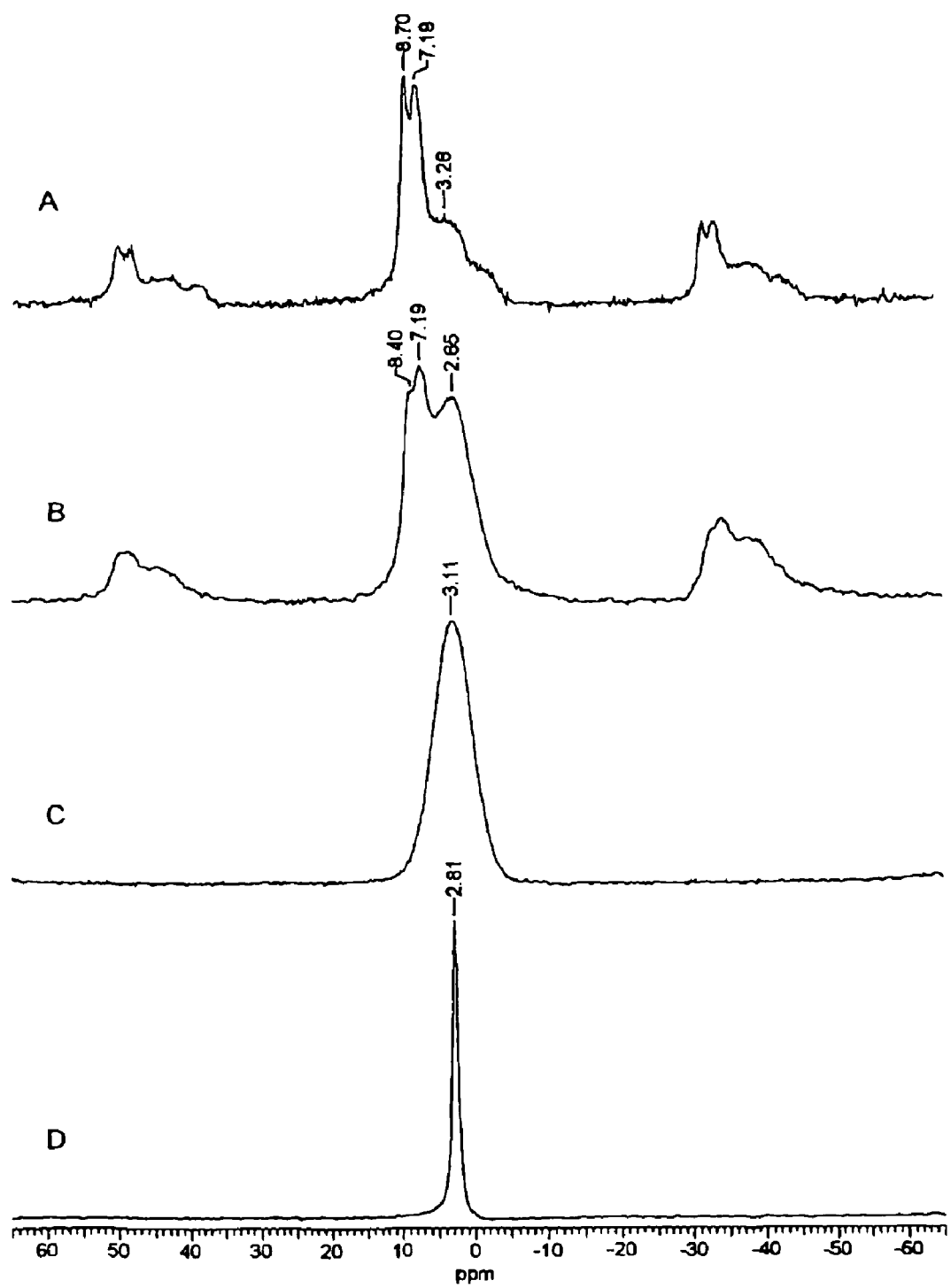
FIG. 14 shows solid-state $^{31}P$ NMR of hydroxyapatite precursor phases heated at: A-130° C. 48H, B-250° C. 24 h, C-300° C. 24 h and D 700° C. 24 h.

Without the application of special methods solid-state NMR spectra tend to consist of very broad featureless lines. These result from dipole interactions with protons and from shielding anisotropy (SA). Since the SA reflects the asymmetry of the electron cloud the peak patterns, called spinning side bands, are very sensitive to the symmetry of the molecule. All of the spectra at relatively low temperatures show intensive spinning sidebands, which are indicative that phosphorous containing units are protonated (FIGS. 14A, B). For instance, the $PO_4^{3-}$ ion in hydroxyapatite shows a very weak side bands pattern, whereas $HPO_4^{2-}$ in a brushite ($CaHPO_4 \times 2HH_2O$) shows very strong one.

All solid-state samples heated at low temperatures (130-250° C.) have line widths ($\Delta vv_{1/2}$) up to 500 Hz indicating that they are amorphous. A decrease of line-width resulting from the increased temperature of heat treatment was observed demonstrating a growth in crystallinity (FIGS. 14C, D) heat treated at 700° C. shows the narrowest line and is thus the most crystalline. However, it should be noted that the line width would have to fall below 100 Hz before it could be considered to be well crystallized HAp.

Hydroxyapatite Formation (300-900° C.)

Phosphate Bands $PO_4^{3-}$ and O—H Stretching Vibrations

The infrared absorption spectra of biological apatites display characteristic bands due to $OH^-$, $PO_4^{3-}$ and $CO_3^{2-}$ (FIGS. 15A-C). Most of the stoichiometric synthetic HAp shows bands due to OH and $PO_4^{3-}$ groups only. The most intense bands associated with $PO_4^{2-}$ vibrations in calcium phosphate materials are the asymmetric stretching mode at 1100-1000 cm–1 ($v_3$ band) and the asymmetrical bending mode at 600-550 $cm^{-1}$ ($v_4$ band). The main characteristic infrared bands of the $PO_4^{3-}$ group occur at 1088, 1043, 962 and in the region 600-460 $cm^1$ The strong peak at 3572 $cm^{-1}$ confirms the presence of $OH^-$ ions in the apatite crystal lattice. This mode is due to the characteristic O—H stretching mode of hydroxyl ion vibrations in the crystal. The O—H liberation at 631 $cm^{-1}$ modes is missing in bone pattern, but present in synthetic HAp although OH is present in both materials.

Carbonate Anion $CO_3^{2-}$

Figure 15:
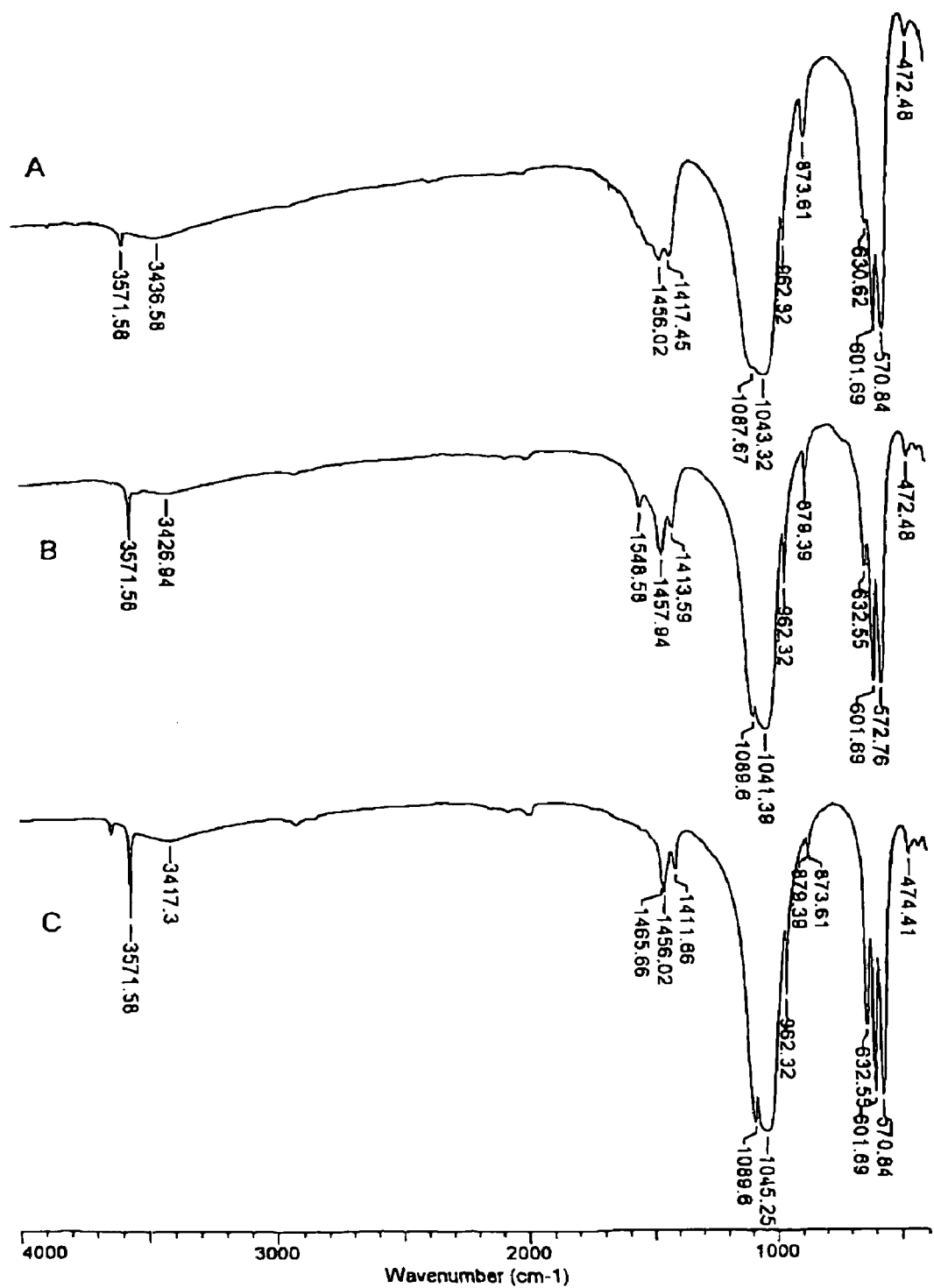
FIG. 15 shows FT-IR spectra of mixed solid calcium diacetyl hydrogen phosphonate precursor according to the preferred embodiment of the sixth aspect of the invention.

Carbonate ion is the main impurity in biological apatites, and much evidence exists to show that $CO_3^{2-}$ substitutes for $PO_4^{3-}$ in the crystal lattice. Biogenic apatites show characteristic absorption bands near 1450, 1410 and 870 $cm^{-1}$ resulting from the presence of carbonate ions. The spectrum of pure HAp lacks the bands at 860-880 $cm^{-1}$, however the spectrum of mature bone does have a peak at 874 $cm^{-1}$ that has been assigned to $CO_3^{2-}$ $v_2$-bending mode of dahllite (B-type carbonated HAp, $CO_3$-for-$PO_4$ substitution). Carbonate pattern starts to appear after heat treatment at 500° C. 24 h at 1456, 1417 and 874 $cm^{-1}$ (FIG. 15A). The appearance of $v_2$ doublets at 874 and 879 $cm^{-2}$ in the spectra of biogenic and present apatites has been explained as indicating the $CO_3^{2-}$ to be present in two different environments (A and B type carbonated apatites). The samples heated up to 700° C. are nixed A, B type carbonated hydroxyapatite that is revealed by $v_3$ carbonate bands at 1548 and 1458 $cm^{-1}$, which corresponds to type A ($CO_3$-for-OH substitution) carbonate, and those at 1460-shoulder and 1414 $cm^{-1}$, which correspond to type B carbonate (spectrum B in FIG. 15). The bands at 879 and 874 $cm^{-1}$ are assigned to $v_2$ modes of type A and B carbonates, respectively (spectrum C in FIG. 15). When the temperature is increased these carbonate bands become less intensive, while band corresponding to liberation mode of O—H at groups 633 $cm^{-1}$ become more intensive.

Here the presence of carbonate vibrations verify that the hydroxyapatite is B type one resembling human bone.

DTA/TG and XRD

The TG profile a sol aged at 70° C. 48 h and solidified at 130° C. 48 h (FIG. 16A) indicated a total weight loss of 38% from ambient to 1000° C. The TG graph includes two steps: an initial weight loss (35%) that occurred from ambient to 420° C. and a smaller one (396) that occurred from 420 to 1000° C. The initial weight loss is due to evaporation of absorbed water, oxidation of the residual solvents and vigorous decomposition of the organic-inorganic precursor at 418° C. Since there are no other exothermic peaks it may be concluded that the formation of poorly crystallized HAp occurs at the same temperature, which slowly releases carbon dioxide with the increase of the temperature (see also FIGS. 15A, B and C).

Figure 16:
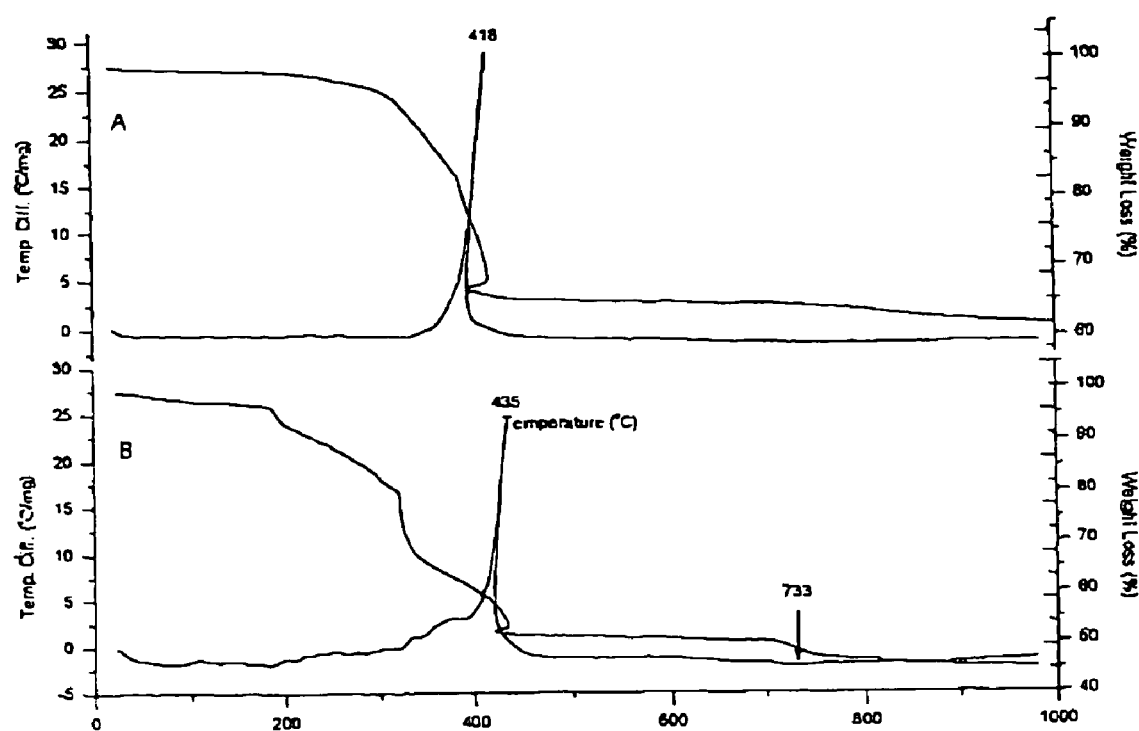
FIG. 16 shows DTA/TG analysis of powders obtained from, A-sol aged at 70° C. 48 h. B-sol aged at ambient temperature 48 h. Both sols were solidified at 130° C. after ageing.
Figure 17:
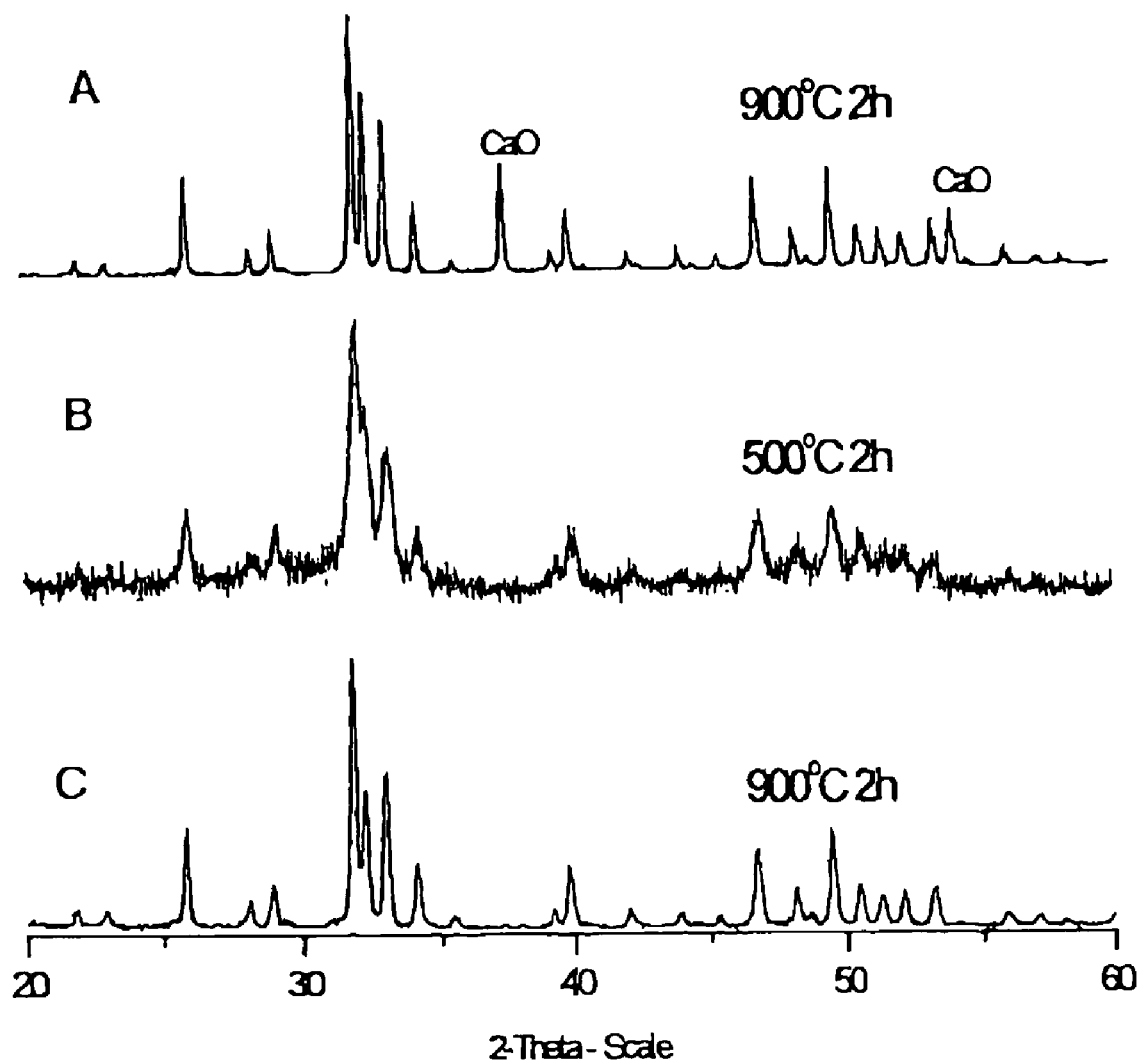
FIG. 17 shows XRD patterns of hydroxyapatite obtained from: B and C-sol aged at 70° C. 48 h, solidified at 130° C. and fired at 500° C. 2 h and at 900° C. 2 h, respectively according to a preferred embodiment of the tenth aspect of the invention. A-sol aged at ambient temperature 48 h and after solidifying fired at 900° C. 2 h. Note the large amounts of CaO observed in spectrum A.

The XRD patterns show the formation of monophasic HAp occurring at temperatures at, and above 500° C. (FIGS. 17B and C). A third XRD pattern represents sol that after 48 h at ambient temperature (corresponds to spectrum C in FIG. 16) was dried at 130° C. and fired at 900° C. so as to avoid chemical reactions occurring in liquid state at temperatures up to 70° C. (FIG. 17A). It should be noted that if the sol is not "aged" the loss of phosphorous occurs resulting in a final product that is not monophasic and the production of calcium oxide. The only difference observed is the existence of large amounts of CaO together with HAp suggesting non-stoichiometry due to loss of phosphorous precursor. The most striking difference from DTA/TG measurements is the endothermic peak at 730° C. and the weight loss at this temperature, most probably originating from decomposition of calcium carbonate formed after the oxidation of the mixed organic precursor at 435° C. (FIG. 16B). These findings show the importance of controlling the processes that occur in liquid state.

It is worth recalling the term "ageing of a sol" which is widely used in sol gel chemistry. In our research, this refers to the time required for ligand substitution ethoxy groups are replaced by acetate ones. The spectroscopic data revealed that under these conditions the ligand exchange is far from completion and the initial phosphorous precursor remained unchanged. However, it is logical to assume that during solidifying of the sol (aged at ambient temperature) at 130° C., a large proportion of the phosphorous precursor is converted into diacetyl hydrogen-phosphonate. Nevertheless, this transformation is not quantitative, therefore some of the phosphorous precursor is lost in the course of this stage, which results in relative increase of Ca/P ratio, and therefore CaO exists in hydroxyapatite phase (FIGS. 16B and 17A). The presence of CaO is often observed in sol-gel derived hydroxyapatite, which is most probably as a result of loss of phosphorous precursor during processing of the solution and hence, increase of the relative Ca/P mol ratio.

CONCLUSIONS

The above experiments illustrate the combined application of FT-IR and NMR spectroscopy to investigate the early stages of hydroxyapatite formation in liquid and solid state. It was proven that the time limitation period: so-called "ageing period" is connected with ligand exchange between ethoxy groups of phosphonate and acetate anions from acetic acid and subsequent chelation with $Ca^{2+}$ ions. The chelation of calcium ions with the diacetyl hydrogen-phosphonate occurs at carbonyl and phosphoryl oxygens of the mixed diacetyl hydrogen phosphonate anhydride. However, the possibility of calcium ions interacting with anhydride oxygen due to reduced solvent polarity cannot be excluded (Structure 5B in FIG. 10). Once formed, these chelates are particularly stable owing to the charge neutralization within the complex. These complexes of calcium with diacetyl phosphonate formed in situ are responsible for the stability of the mixed hydroxyapatite precursor which allow the correct Ca/P ratio of 1.67 to be maintained until the decomposition of the solid precursor and subsequent hydroxyapatite formation. The resulting phase after heat treatment at temperatures ranging from 500 to 1000° C. was monophasic, bone-like (nanosized, plate like, B type carbonate containing) hydroxyapatite. These samples were not accompanied by any detectable levels of additional phases such as CaO and/or β-TCP which are usually present in sol-gel derived powders and coatings. The formation of six-membered chelates may also be assumed for the other divalent metal ions under conditions of lower solvent polarity and reduced solvating properties than water. The isolation and purification of such anhydride substrates via biologically relevant metal ions for instance: Ca2+, Mg2+, Cu2+ and Zn2+ would be of biological interest.

It will be appreciated by persons skilled in the eat that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A process for coating an object with a divalent metal phosphate, the process comprising the steps of:
   (a) preparing a sol containing a divalent metal phosphonate complex wherein a divalent metal is coordinated to a phosphonate compound according to formula (1)

R—C(O)—O—P(O)R¹—O—C(O)—.R²  (1)

wherein R, R¹ and R², which may be the same or different, are selected from the group consisting of hydrogen, substituted alkyl groups and unsubstituted alkyl groups; and
   (b) dipping the object into the sol;
   (c) heating the dipped object in order to remove any solvent; and
   (d) firing the heated object to allow conversion of the divalent metal phosphonate complex into the divalent metal phosphate.

2. The process of claim 1, wherein R and R² are CH₃.

3. The process of claim 1, wherein R¹ is hydrogen.

4. The process of claim 1, wherein the divalent metal is selected from the group consisting of calcium, magnesium, strontium, copper, manganese and zinc.

5. The process of claim 4, wherein the divalent metal is calcium.

6. The process of claim 1, wherein the divalent metal is coordinated with a carbonyl and/or phosphoryl oxygen of the phosphonate.

7. The process of claim 1, wherein the divalent metal phosphonate is a six-membered chelate ring according to formula (2) or (3)

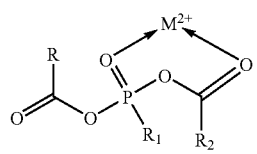

(2)

-continued

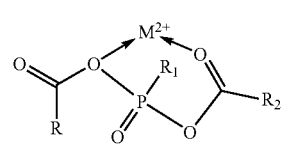

(3)

wherein M²⁻ is a divalent metal and R, R¹ and R²⋅ which may be the same or different, are selected from the group consisting of hydrogen, substituted alkyl groups and unsubstituted alkyl groups.

8. The process of claim 1, wherein the divalent metal phosphonate complex has a structure according to formula (4) or (5)

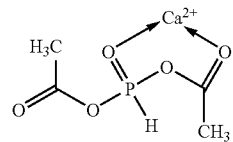

(4)

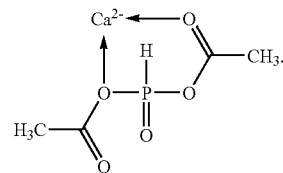

(5)

9. The process according to claim 1, wherein the object is formed from the group consisting of one or more of coral, hydroxyapatite converted from coral, hydroxyapatite, titanium, cobalt, chromium, molybdenum, vitallium alloy, zirconium, alloys, surgical stainless steels, alumina (Al₂O₃), zirconia (PSZ), silicon nitride (Si₃N₄), sialons and bioglasses.

10. The process according to claim 1, wherein the coating covers meso- and nano-pores of the object.

11. The process according to claim 1, wherein in step (c) the object is heated to between about 20° C. and 200° C.

12. The process of claim 11, wherein in step (c) the object is heated to about 130° C.

13. The process according to claim 1, wherein in step (d), the object is fired at between about 500° C. and 1200° C.

14. The process according to claim 1, further comprising incorporating one or more pharmaceutically active compounds in the coating.

15. The process according to claim 1, wherein the pharmaceutically active compounds are selected from the group consisting of bone morphogenic proteins (BMP), collagen, growth factors (GF), and marrow stromal cells (MSC).

* * * * *